United States Patent
Sheppard et al.

(10) Patent No.: US 6,372,889 B1
(45) Date of Patent: Apr. 16, 2002

(54) SOLUBLE PROTEIN ZTMPO-1

(75) Inventors: Paul O. Sheppard, Redmond; Darrell C. Conklin; Theresa M. Farrah, both of Seattle; Mark F. Maurer, Bellevue; Angelika Grossmann, Seattle, all of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/294,531

(22) Filed: Apr. 19, 1999

Related U.S. Application Data

(60) Provisional application No. 60/082,513, filed on Apr. 21, 1998.

(51) Int. Cl.[7] ................................................ C07K 14/47
(52) U.S. Cl. ........................................................ 530/350
(58) Field of Search ............................. 530/350; 514/12

(56) References Cited

FOREIGN PATENT DOCUMENTS

WO          95/17205          6/1995

OTHER PUBLICATIONS

Caldwell, Yakubutsu Dotai (Xenobiotic metabolism and Disposition), vol. 11(1): pp. 119–125, 1996.*

Ohara et al., DNA Res. 5:169–76, 1998. Accession #AB014592.

Nagana et al., Nature Genetics 12:254–259, 1996.

Bione et al., Nature Genetics: 8:323–327, 1994.

Manilal et al., Human Molecular Genetics 5: 801–808, 1996.

Mora et al., Annals of Neurol. 42:249–253, 1997.

Harris et al., Proc. Natl. Acad. Sci. USA 91: 6283–6287, 1994.

Berger et al., Genome Res. 6:361–370, 1996.

Hesslein & Campbell, Molecular & Biochemical Parasitology 86: 121–126, 1997.

Michaely & Vann Bennett, J. Biol. Chem. 268: 22703–22709, 1993.

Adams et al., Nature 355: 632–4, 1992, EST 419.

Adams et al., Nature Genetics 4: 373–380, 1993, EST 27636.

* cited by examiner

*Primary Examiner*—Terry McKelvey
(74) *Attorney, Agent, or Firm*—Susan E. Lingenfelter

(57) ABSTRACT

The present invention relates to polynucleotide and polypeptide molecules for ZTMPO-1, a novel soluble protein with homology to emerin and the thymopoietins. The polypeptides, and polynucleotides encoding them are useful for modulating cellular proliferation and differentiation and may be used for diagnostic purposes. The present invention also includes antibodies to the ZTMPO-1 polypeptides.

5 Claims, 3 Drawing Sheets

```
EMD_HU : ------------------------------------------------------------------------------ ;   0
ZTMPO1 : ------------------------------------------------------------------------------ ;   0
PIR_A5 : MPEFLEDPSVLTKDKLKSELVANNVTLPAGEQRKDVVYVQLYLQHLTARNRPPLPAGTNSKGPPDFSSDEEREPTP   ;  75
PIR_B5 : MPEFLEDPSVLTKDKLKSELVANNVTLPAGEQRKDVVYVQLYLQHLTARNRPPLPAGTNSKGPPDFSSDEEREPTP   ;  75
PIR_C5 : MPEFLEDPSVLTKDKLKSELVANNVTLPAGEQRKDVVYVQLYLQHLTARNRPPLPAGTNSKGPPDFSSDEEREPTP   ;  75

EMD_HU : ----------------MDNYADLSDTELTTLLRRYNIPHGPVVGSTRRLYEKKIFEYE                      ;  42
ZTMPO1 : ----------------MTMDALLARLKLLNPDDLREEIVKAGLKCGPITSTTRFIFEKKLAQAL                ;  48
PIR_A5 : VLGSGAAAAGRSRAAVGRKATKKTDKPRQEDKDDLDVTELTNEDLLDQLVKYGVNPGPIVGTTRKLYEKKLLKLR    ; 150
PIR_B5 : VLGSGAAAAGRSRAAVGRKATKKTDKPRQEDKDDLDVTELTNEDLLDQLVKYGVNPGPIVGTTRKLYEKKLLKLR    ; 150
PIR_C5 : VLGSGAAAAGRSRAAVGRKATKKTDKPRQEDKDDLDVTELTNEDLLDQLVKYGVNPGPIVGTTRKLYEKKLLKLR    ; 150

EMD_HU : TQRR-RLSPPSSAASSYSFSDLNSTRGDADMYDLPKKEDAL------------                            ;  83
ZTMPO1 : LEQGGRLSSFYHHEAGVTALSQDPQRILKPAEGNPTDQAGFS-----                                 ;  90
PIR_A5 : EQGTESRSSTPLPTISSSAENTRQNGSNDSDRYSDNEEGKKK                                      ; 192
PIR_B5 : EQGTESRSSTPLPTISSSAENTRQNGSNDSDRYSDNEEDSKIELKLEKREPLKGRAKTPVTLKQRRVEHNQSYSQ    ; 225
PIR_C5 : EQGTESRSSTPLPTISSSAENTRQNGSNDSDRYSDNEEDSKIELKLEKREPLKGRAKTPVTLKQRRVEHNQ---    ; 221

EMD_HU : -----------LYQSKGYNDDYYEESYFTTRTYGEPESAGPSRAVRQSVTSFPDA                         ; 127
ZTMPO1 : -----------EDRDFGYSVGLNPPEEEAVTSKTCSVPPSDTDTYRAGATASKEP                         ; 134
PIR_A5 : -----------EHKKVKSTRDIVPFSELGTTPSGGGFFQGISFPEISTRPPLGST                         ; 236
PIR_B5 : AGITETEWTSGSSKGGPLQALTRESTRGSRRTPRKRVETSEHFRIDGPVISESTPIAETIMASSNESLVVNRVTG    ; 300
PIR_C5 : ----------------------------------------------------------                      ; 221

EMD_HU : DAFHHQVHDDDLLSSEEECKDRERPMYGRDSAYQSITHYRPVSASRSSLDLSYYPTSSSTSFMSSSSSSSWLT       ; 202
ZTMPO1 : PLYYGVCPVYEDVPARNERIYYENKKEALQAVKMIKGSRFKAFSTREDAEKFARGICDYFPSPSKTSLPLSPVK     ; 209
PIR_A5 : ELQAAKKVHTSKGDLPREPLVATNLPGRGQLQKLASERNLFISCKSSHDRCLEKSSSSSQPEHSAMLVSTAASP     ; 311
PIR_B5 : NFKHASPILPITEFSDIPRRAPKKPLTRAEVGEKTEERRVERDILKEMFPYEASTPTGISASCRRPIKGAAGRPL    ; 375
PIR_C5 : -----------------------VGEKTEERRVERDILKEMFPYEASTPTGISASCRRPIKGAAGRPL           ; 266

EMD_HU : RR-----------AIRPENRAPGAGLGQDRQVPLWGQLLLFLVFIVLFFIYHFMQAEEGNPF------           ; 254
ZTMPO1 : TAPLFSNDRLKDGLCLSESETVNKERANSYKNPRTQDLTAKLRKAVEKGEEDTFSDLIWSNPRYLIGSGDNPTIV     ; 284
PIR_A5 : SLIKETTTGYYKDIVENICGREKSGIQPLCPERSHISDQSPLSSKRKALEESESSQLISPPLAQAIRDYVNSLLV     ; 386
PIR_B5 : ELSDFRMEESFSSKYVPKYVPLADVKSEKTKKGRSIPVWIKILLFVVVAVFLFVYQAMETNQVNPFSNFLHVDP      ; 450
PIR_C5 : ELSDFRMEESFSSKYVPKYVPLADVKSEKTKKGRSIPVWIKILLFVVVAVFLFVYQAMETNQVNPFSNFLHVDP      ; 341
```

```
EMD_HU:   ------------------------------------------------------                              ; 254
ZTMPO1:   QEGCRYNVMHVAAKENQASICQLTLDVLENPDFMRLMYPDDDEAMLQKRIRYVVDLYLNTPDKMGYDTPLHFACK         ; 359
PIR_A5:   QGGVGSLPGTSNSMPPLDVENIQKRIDQSKFQET-EFLSPPRKVPRLSEKSVEERDSGSFVAFQNIPGSELMSSF         ; 460
PIR_B5:   RKSN------------------------------------------------------------------------         ; 454
PIR_C5:   RKSN------------------------------------------------------------------------         ; 345

EMD_HU:   ------------------------------------------------------                              ; 254
ZTMPO1:   FGNADVVNVLSSHHLIVKNSRNKYDKTPEDVICERSKNKSVELKERIREYLKGHYYVPLLRAEETSSPVIGELWS         ; 434
PIR_A5:   AKTVVSHSLTTLGLEVAKQSQHDKIDASBLSFPFHESILKVIEEEWQQVDRQLPSLACKYPVSSREATQILSVPK         ; 535
PIR_B5:   ---------------------------------------------------------------------------         ; 454
PIR_C5:   ---------------------------------------------------------------------------         ; 345

EMD_HU:   ------------------------------------------------------                              ; 254
ZTMPO1:   PDQTAEAASHVSRYGGSPRDPVLTLRAFAGPLSPAKAEDFRKLWKTPPREKAGFLHHVKKSDPERGFERVGRELAH         ; 509
PIR_A5:   VDDEILGFISEATPLGGIQAASTESCNQQLDLALCRAYEAAASALQIATHTAFVAKAMQADISQAAQILSSDPSR         ; 610
PIR_B5:   ---------------------------------------------------------------------------         ; 454
PIR_C5:   ---------------------------------------------------------------------------         ; 345

EMD_HU:   ------------------------------------------------------                              ; 254
ZTMPO1:   ELGYPWVEYWEFLGCFVDLSSQEGLQRLEEYLTQQEIGKKAQQETGEREASCRDKATTSGSNSISVRAFLDEDDM         ; 584
PIR_A5:   THQALGILSKTYDAASYICEAAFDEVKMAAHTMGNATVGRRYLWLKDCKINLASKNKLASTPFKGGTLFGGEVCK         ; 685
PIR_B5:   ---------------------------------------------------------------------------         ; 454
PIR_C5:   ---------------------------------------------------------------------------         ; 345

EMD_HU:   ------------------------------------------------------                              ; 254
ZTMPO1:   SLEEIKNRQNAARNNSPPTVGAFGHTRCSAFPLEQEADLIEAAEPGGPHSSRNGLCHPLNHSRTLAGKRPKAPHG         ; 659
PIR_A5:   VIKKRGNKH------------------------------------------------------------------         ; 694
PIR_B5:   ---------------------------------------------------------------------------         ; 454
PIR_C5:   ---------------------------------------------------------------------------         ; 345

EMD_HU:   ------------------------------------------------------                              ; 254
ZTMPO1:   EEAHLPPVSDLTVEFDKLNLQNIGRSVSKTPDESTKTKDQILTSRINAVERDLLEPSPADQLGNGHRRTESEMSA         ; 734
PIR_A5:   ---------------------------------------------------------------------------         ; 694
PIR_B5:   ---------------------------------------------------------------------------         ; 454
PIR_C5:   ---------------------------------------------------------------------------         ; 345
```

```
EMD_HU    : ------------------------------------------------------ ;
ZTMPO1    : RIAKMSLSPSSPRHEDQLEVTREPARRLFLFGEEPSKLDQDVLAALECADVDPHQFPAVHRWKSAVLCYSPSDRQ ; 809
PIR_A5    : ------------------------------------------------------ ; 694
PIR_B5    : ------------------------------------------------------ ; 454
PIR_C5    : ------------------------------------------------------ ; 345

EMD_HU    : ------------------------------------------------------ ; 254
ZTMPO1    : SWPSPAVKGRFKSQLPDLSGPHSYSPGRNSVAGSNPAKPGLGSPGRYSPVHGSQLRRMARLAELAAL--- ; 876
PIR_A5    : ------------------------------------------------------ ; 694
PIR_B5    : ------------------------------------------------------ ; 454
PIR_C5    : ------------------------------------------------------ ; 345
```

FIGURE

SEQUENCE LISTING

<160> NUMBER OF SEQ ID NOS: 35

<210> SEQ ID NO 1
<211> LENGTH: 2884
<212> TYPE: DNA
<213> ORGANISM: Homo sapiens
<220> FEATURE:
<221> NAME/KEY: CDS
<222> LOCATION: (127)...(2754)

<400> SEQUENCE: 1

```
aaagttttta atgaaagaaa cagaaactga tgccattata taatgaaccc tagtacccat      60
cacccagctt cagcaggtgt tagtattttg tgactctttg atttttttgt cttgggccta     120 ggtgaa atg aca atg gat gct ctg ttg gct cga ttg aaa ctt ctg aat      168
       Met Thr Met Asp Ala Leu Leu Ala Arg Leu Lys Leu Leu Asn
         1               5                  10 cca gat gac ctt aga gaa gaa atc gtc aaa gcc gga ttg aaa tgt gga   216
Pro Asp Asp Leu Arg Glu Glu Ile Val Lys Ala Gly Leu Lys Cys Gly
 15                  20                  25                  30 ccc att aca tca act aca agg ttc att ttt gag aaa aaa ttg gct cag   264
Pro Ile Thr Ser Thr Thr Arg Phe Ile Phe Glu Lys Lys Leu Ala Gln
                 35                  40                  45
```

-continued

| | |
|---|---|
| gct tta ctg gag caa gga gga agg ctg tct tct ttc tac cac cat gag<br>Ala Leu Leu Glu Gln Gly Gly Arg Leu Ser Ser Phe Tyr His His Glu<br>            50                        55                        60 | 312 |
| gca ggt gtc aca gct ctc agc cag gac cca caa agg att ttg aag cca<br>Ala Gly Val Thr Ala Leu Ser Gln Asp Pro Gln Arg Ile Leu Lys Pro<br>        65                        70                        75 | 360 |
| gct gaa ggg aac cca act gat cag gct ggt ttt tct gaa gac aga gat<br>Ala Glu Gly Asn Pro Thr Asp Gln Ala Gly Phe Ser Glu Asp Arg Asp<br>80                          85                        90 | 408 |
| ttt ggt tac agt gtg ggc ctg aat cct cca gag gag gaa gct gtg aca<br>Phe Gly Tyr Ser Val Gly Leu Asn Pro Pro Glu Glu Glu Ala Val Thr<br>95                      100                 105               110 | 456 |
| tcc aag acc tgc tcg gtg ccc cct agt gac acc gac acc tac aga gct<br>Ser Lys Thr Cys Ser Val Pro Pro Ser Asp Thr Asp Thr Tyr Arg Ala<br>              115                 120               125 | 504 |
| gga gcg act gcg tct aag gag ccg ccc ctg tac tat ggg gtg tgt cca<br>Gly Ala Thr Ala Ser Lys Glu Pro Pro Leu Tyr Tyr Gly Val Cys Pro<br>            130                 135               140 | 552 |
| gtg tat gag gac gtc cca gcg aga aat gaa agg atc tat gtt tat gaa<br>Val Tyr Glu Asp Val Pro Ala Arg Asn Glu Arg Ile Tyr Val Tyr Glu<br>   145                     150               155 | 600 |
| aat aaa aag gaa gca ttg caa gct gtc aag atg atc aaa ggg tcc cga<br>Asn Lys Lys Glu Ala Leu Gln Ala Val Lys Met Ile Lys Gly Ser Arg<br>160                          165               170 | 648 |
| ttt aaa gct ttt tct acc aga gaa gac gct gag aaa ttt gct aga gga<br>Phe Lys Ala Phe Ser Thr Arg Glu Asp Ala Glu Lys Phe Ala Arg Gly<br>175                          180               185               190 | 696 |
| att tgt gat tat ttc cct tct cca agc aaa acg tcc tta cca ctg tct<br>Ile Cys Asp Tyr Phe Pro Ser Pro Ser Lys Thr Ser Leu Pro Leu Ser<br>                   195               200               205 | 744 |
| cct gtg aaa aca gct cca ctc ttt agc aat gac agg ttg aaa gat ggt<br>Pro Val Lys Thr Ala Pro Leu Phe Ser Asn Asp Arg Leu Lys Asp Gly<br>            210                 215               220 | 792 |
| ttg tgc ttg tcg gaa tca gaa aca gtc aac aaa gag cga gcg aac agt<br>Leu Cys Leu Ser Glu Ser Glu Thr Val Asn Lys Glu Arg Ala Asn Ser<br>              225                 230               235 | 840 |
| tac aaa aat ccc cgc acg cag gac ctc acc gcc aag ctt cgg aaa gct<br>Tyr Lys Asn Pro Arg Thr Gln Asp Leu Thr Ala Lys Leu Arg Lys Ala<br>240                          245               250 | 888 |
| gtg gag aag gga gag gag gac acc ttt tct gac ctt atc tgg agc aac<br>Val Glu Lys Gly Glu Glu Asp Thr Phe Ser Asp Leu Ile Trp Ser Asn<br>255                          260               265               270 | 936 |
| ccc cgg tat ctg ata ggc tca gga gac aac ccc act atc gtg cag gaa<br>Pro Arg Tyr Leu Ile Gly Ser Gly Asp Asn Pro Thr Ile Val Gln Glu<br>                 275               280               285 | 984 |
| ggg tgc agg tac aac gtg atg cat gtt gct gcc aaa gag aac cag gct<br>Gly Cys Arg Tyr Asn Val Met His Val Ala Ala Lys Glu Asn Gln Ala<br>            290                 295               300 | 1032 |
| tcc atc tgc cag ctg act ctg gac gtc ctg gag aac cct gac ttc atg<br>Ser Ile Cys Gln Leu Thr Leu Asp Val Leu Glu Asn Pro Asp Phe Met<br>              305                 310               315 | 1080 |
| agg ctg atg tac cct gat gac gac gag gcc atg ctg cag aag cgt atc<br>Arg Leu Met Tyr Pro Asp Asp Asp Glu Ala Met Leu Gln Lys Arg Ile<br>320                          325               330 | 1128 |
| cgt tac gtg gtg gac ctg tac ctc aac acc ccc gac aag atg ggc tat<br>Arg Tyr Val Val Asp Leu Tyr Leu Asn Thr Pro Asp Lys Met Gly Tyr<br>335                          340               345               350 | 1176 |
| gac aca ccg ttg cat ttt gct tgt aag ttt gga aat gca gat gta gtc<br>Asp Thr Pro Leu His Phe Ala Cys Lys Phe Gly Asn Ala Asp Val Val<br>              355                 360               365 | 1224 |

```
aac gtg ctt tcg tca cac cat ttg att gta aaa aac tca agg aat aaa   1272
Asn Val Leu Ser Ser His His Leu Ile Val Lys Asn Ser Arg Asn Lys
            370                 375                 380 tat gat aaa aca cct gaa gat gta att tgt gaa aga agc aaa aat aaa   1320
Tyr Asp Lys Thr Pro Glu Asp Val Ile Cys Glu Arg Ser Lys Asn Lys
        385                 390                 395 tct gtg gaa ctg aag gag cgg atc aga gag tat tta aag ggc cac tac   1368
Ser Val Glu Leu Lys Glu Arg Ile Arg Glu Tyr Leu Lys Gly His Tyr
    400                 405                 410 tac gtg ccc ctc ctg aga gcg gaa gag act tct tct cca gtc atc ggg   1416
Tyr Val Pro Leu Leu Arg Ala Glu Glu Thr Ser Ser Pro Val Ile Gly
415                 420                 425                 430 gag ctg tgg tcc cca gac cag acg gct gag gcc tct cac gtc agc cgc   1464
Glu Leu Trp Ser Pro Asp Gln Thr Ala Glu Ala Ser His Val Ser Arg
                435                 440                 445 tat gga ggc agc ccc aga gac ccg gta ctg acc ctg aga gcc ttc gca   1512
Tyr Gly Gly Ser Pro Arg Asp Pro Val Leu Thr Leu Arg Ala Phe Ala
            450                 455                 460 ggg ccc ctg agt cca gcc aag gca gaa gat ttt cgc aag ctc tgg aaa   1560
Gly Pro Leu Ser Pro Ala Lys Ala Glu Asp Phe Arg Lys Leu Trp Lys
        465                 470                 475 act cca cct cga gag aaa gca ggc ttc ctt cac cac gtc aag aag tcg   1608
Thr Pro Pro Arg Glu Lys Ala Gly Phe Leu His His Val Lys Lys Ser
    480                 485                 490 gac ccg gaa aga ggc ttt gag aga gtg gga agg gag cta gct cat gag   1656
Asp Pro Glu Arg Gly Phe Glu Arg Val Gly Arg Glu Leu Ala His Glu
495                 500                 505                 510 ctg ggg tat ccc tgg gtt gaa tac tgg gaa ttt ctg ggc tgt ttt gtt   1704
Leu Gly Tyr Pro Trp Val Glu Tyr Trp Glu Phe Leu Gly Cys Phe Val
                515                 520                 525 gat ctg tct tcc cag gaa ggc ctg caa aga cta gaa gaa tat ctc aca   1752
Asp Leu Ser Ser Gln Glu Gly Leu Gln Arg Leu Glu Glu Tyr Leu Thr
            530                 535                 540 cag cag gaa ata ggc aaa aag gct caa caa gaa aca gga gaa cgg gaa   1800
Gln Gln Glu Ile Gly Lys Lys Ala Gln Gln Glu Thr Gly Glu Arg Glu
        545                 550                 555 gcc tcc tgc cga gat aaa gcc acc acg tct ggc agc aat tcc att tcc   1848
Ala Ser Cys Arg Asp Lys Ala Thr Thr Ser Gly Ser Asn Ser Ile Ser
    560                 565                 570 gtg agg gcg ttt cta gat gaa gat gac atg agc ttg gaa gaa ata aaa   1896
Val Arg Ala Phe Leu Asp Glu Asp Asp Met Ser Leu Glu Glu Ile Lys
575                 580                 585                 590 aat cgg caa aat gca gct cga aat aac agc ccg ccc aca gtc ggt gct   1944
Asn Arg Gln Asn Ala Ala Arg Asn Asn Ser Pro Pro Thr Val Gly Ala
                595                 600                 605 ttt gga cat acg agg tgc agc gcc ttc ccc ttg gag cag gag gca gac   1992
Phe Gly His Thr Arg Cys Ser Ala Phe Pro Leu Glu Gln Glu Ala Asp
            610                 615                 620 ctc ata gaa gcc gcc gag ccg gga ggt cca cac agc agc aga aat ggg   2040
Leu Ile Glu Ala Ala Glu Pro Gly Gly Pro His Ser Ser Arg Asn Gly
        625                 630                 635 ctc tgc cat cct ctg aat cac agc agg acc ctg gcg ggc aag aga cca   2088
Leu Cys His Pro Leu Asn His Ser Arg Thr Leu Ala Gly Lys Arg Pro
    640                 645                 650 aag gcc ccc cat ggg gag gaa gcc cat ctg cca cct gtc tcg gat ttg   2136
Lys Ala Pro His Gly Glu Glu Ala His Leu Pro Pro Val Ser Asp Leu
655                 660                 665                 670 act gtt gag ttt gat aaa ctg aat ttg caa aat ata gga cgt agc gtt   2184
Thr Val Glu Phe Asp Lys Leu Asn Leu Gln Asn Ile Gly Arg Ser Val
```

-continued

```
            675                 680                 685
tcc aag aca cca gat gaa agt aca aaa act aaa gat cag atc ctg act    2232
Ser Lys Thr Pro Asp Glu Ser Thr Lys Thr Lys Asp Gln Ile Leu Thr
                690                 695                 700 tca aga atc aat gca gta gaa aga gac ttg tta gag cct tct ccc gca    2280
Ser Arg Ile Asn Ala Val Glu Arg Asp Leu Leu Glu Pro Ser Pro Ala
            705                 710                 715 gac caa ctc ggg aat ggc cac agg agg aca gaa agt gaa atg tca gcc    2328
Asp Gln Leu Gly Asn Gly His Arg Arg Thr Glu Ser Glu Met Ser Ala
        720                 725                 730 agg atc gct aaa atg tcc ttg agt ccc agc agc ccc agg cac gag gat    2376
Arg Ile Ala Lys Met Ser Leu Ser Pro Ser Ser Pro Arg His Glu Asp
735                 740                 745                 750 cag ctc gag gtc acc agg gaa ccg gcc agg cgg ctc ttc ctt ttt gga    2424
Gln Leu Glu Val Thr Arg Glu Pro Ala Arg Arg Leu Phe Leu Phe Gly
                755                 760                 765 gag gag cca tca aaa ctc gat cag gat gtt ttg gcc gct ctt gaa tgt    2472
Glu Glu Pro Ser Lys Leu Asp Gln Asp Val Leu Ala Ala Leu Glu Cys
            770                 775                 780 gca gac gtc gac ccc cat cag ttc ccg gcc gtg cac aga tgg aag agt    2520
Ala Asp Val Asp Pro His Gln Phe Pro Ala Val His Arg Trp Lys Ser
        785                 790                 795 gct gtc ctg tgc tac tca ccc tcg gac aga cag agt tgg ccc agt ccc    2568
Ala Val Leu Cys Tyr Ser Pro Ser Asp Arg Gln Ser Trp Pro Ser Pro
800                 805                 810 gcg gtg aaa gga agg ttc aag tct cag ctg cca gat ctc agt ggc cct    2616
Ala Val Lys Gly Arg Phe Lys Ser Gln Leu Pro Asp Leu Ser Gly Pro
815                 820                 825                 830 cac agc tac agt ccg ggg aga aac agc gtg gct gga agc aac ccc gca    2664
His Ser Tyr Ser Pro Gly Arg Asn Ser Val Ala Gly Ser Asn Pro Ala
                835                 840                 845 aag cca ggc ctg ggc agt cct ggg cgc tac agc ccc gtg cac ggg agc    2712
Lys Pro Gly Leu Gly Ser Pro Gly Arg Tyr Ser Pro Val His Gly Ser
            850                 855                 860 cag ctc cgc agg atg gcg cgc ctg gct gag ctt gcc gcc ctg            2754
Gln Leu Arg Arg Met Ala Arg Leu Ala Glu Leu Ala Ala Leu
        865                 870                 875 taggcttggc gctgggctct cggtttgttc ttcatttttta aagaaggaag ggtcatatgt    2814
ttattgctaa actgtcaaaa aggaatatat tctgattaaa ttattactcc tcaaaaaaaa    2874
aaaaaaaaaa                                                            2884

<210> SEQ ID NO 2
<211> LENGTH: 876
<212> TYPE: PRT
<213> ORGANISM: Homo sapiens

<400> SEQUENCE: 2

Met Thr Met Asp Ala Leu Leu Ala Arg Leu Lys Leu Leu Asn Pro Asp
1               5                   10                  15

Asp Leu Arg Glu Glu Ile Val Lys Ala Gly Leu Lys Cys Gly Pro Ile
                20                  25                  30

Thr Ser Thr Thr Arg Phe Ile Phe Glu Lys Lys Leu Ala Gln Ala Leu
            35                  40                  45

Leu Glu Gln Gly Gly Arg Leu Ser Ser Phe Tyr His His Glu Ala Gly
        50                  55                  60

Val Thr Ala Leu Ser Gln Asp Pro Gln Arg Ile Leu Lys Pro Ala Glu
65                  70                  75                  80
```

-continued

```
Gly Asn Pro Thr Asp Gln Ala Gly Phe Ser Glu Asp Arg Asp Phe Gly
                 85                  90                  95

Tyr Ser Val Gly Leu Asn Pro Glu Glu Ala Val Thr Ser Lys
            100                 105                 110

Thr Cys Ser Val Pro Ser Asp Thr Asp Tyr Arg Ala Gly Ala
        115                 120                 125

Thr Ala Ser Lys Glu Pro Pro Leu Tyr Tyr Gly Val Cys Pro Val Tyr
        130                 135                 140

Glu Asp Val Pro Ala Arg Asn Glu Arg Ile Tyr Val Tyr Glu Asn Lys
145                 150                 155                 160

Lys Glu Ala Leu Gln Ala Val Lys Met Ile Lys Gly Ser Arg Phe Lys
                165                 170                 175

Ala Phe Ser Thr Arg Glu Asp Ala Glu Lys Phe Ala Arg Gly Ile Cys
                180                 185                 190

Asp Tyr Phe Pro Ser Pro Ser Lys Thr Ser Leu Pro Leu Ser Pro Val
            195                 200                 205

Lys Thr Ala Pro Leu Phe Ser Asn Asp Arg Leu Lys Asp Gly Leu Cys
    210                 215                 220

Leu Ser Glu Ser Glu Thr Val Asn Lys Glu Arg Ala Asn Ser Tyr Lys
225                 230                 235                 240

Asn Pro Arg Thr Gln Asp Leu Thr Ala Lys Leu Arg Lys Ala Val Glu
                245                 250                 255

Lys Gly Glu Glu Asp Thr Phe Ser Asp Leu Ile Trp Ser Asn Pro Arg
                260                 265                 270

Tyr Leu Ile Gly Ser Gly Asp Asn Pro Thr Ile Val Gln Glu Gly Cys
                275                 280                 285

Arg Tyr Asn Val Met His Val Ala Ala Lys Glu Asn Gln Ala Ser Ile
    290                 295                 300

Cys Gln Leu Thr Leu Asp Val Leu Glu Asn Pro Asp Phe Met Arg Leu
305                 310                 315                 320

Met Tyr Pro Asp Asp Glu Ala Met Leu Gln Lys Arg Ile Arg Tyr
                325                 330                 335

Val Val Asp Leu Tyr Leu Asn Thr Pro Asp Lys Met Gly Tyr Asp Thr
            340                 345                 350

Pro Leu His Phe Ala Cys Lys Phe Gly Asn Ala Asp Val Val Asn Val
        355                 360                 365

Leu Ser Ser His His Leu Ile Val Lys Asn Ser Arg Asn Lys Tyr Asp
370                 375                 380

Lys Thr Pro Glu Asp Val Ile Cys Glu Arg Ser Lys Asn Lys Ser Val
385                 390                 395                 400

Glu Leu Lys Glu Arg Ile Arg Glu Tyr Leu Lys Gly His Tyr Tyr Val
                405                 410                 415

Pro Leu Leu Arg Ala Glu Glu Thr Ser Ser Pro Val Ile Gly Glu Leu
            420                 425                 430

Trp Ser Pro Asp Gln Thr Ala Glu Ala Ser His Val Ser Arg Tyr Gly
        435                 440                 445

Gly Ser Pro Arg Asp Pro Val Leu Thr Leu Arg Ala Phe Ala Gly Pro
    450                 455                 460

Leu Ser Pro Ala Lys Ala Glu Asp Phe Arg Lys Leu Trp Lys Thr Pro
465                 470                 475                 480

Pro Arg Glu Lys Ala Gly Phe Leu His His Val Lys Lys Ser Asp Pro
                485                 490                 495

Glu Arg Gly Phe Glu Arg Val Gly Arg Glu Leu Ala His Glu Leu Gly
```

-continued

```
                    500                 505                 510
        Tyr Pro Trp Val Glu Tyr Trp Glu Phe Leu Gly Cys Phe Val Asp Leu
                    515                 520                 525

Ser Ser Gln Glu Gly Leu Gln Arg Leu Glu Glu Tyr Leu Thr Gln Gln
                    530                 535                 540

Glu Ile Gly Lys Lys Ala Gln Gln Glu Thr Gly Glu Arg Glu Ala Ser
        545                 550                 555                 560

Cys Arg Asp Lys Ala Thr Thr Ser Gly Ser Asn Ser Ile Ser Val Arg
                        565                 570                 575

Ala Phe Leu Asp Glu Asp Asp Met Ser Leu Glu Glu Ile Lys Asn Arg
                        580                 585                 590

Gln Asn Ala Ala Arg Asn Asn Ser Pro Pro Thr Val Gly Ala Phe Gly
                    595                 600                 605

His Thr Arg Cys Ser Ala Phe Pro Leu Glu Gln Glu Ala Asp Leu Ile
                    610                 615                 620

Glu Ala Ala Glu Pro Gly Gly Pro His Ser Ser Arg Asn Gly Leu Cys
        625                 630                 635                 640

His Pro Leu Asn His Ser Arg Thr Leu Ala Gly Lys Arg Pro Lys Ala
                        645                 650                 655

Pro His Gly Glu Glu Ala His Leu Pro Pro Val Ser Asp Leu Thr Val
                    660                 665                 670

Glu Phe Asp Lys Leu Asn Leu Gln Asn Ile Gly Arg Ser Val Ser Lys
                    675                 680                 685

Thr Pro Asp Glu Ser Thr Lys Thr Lys Asp Gln Ile Leu Thr Ser Arg
                    690                 695                 700

Ile Asn Ala Val Glu Arg Asp Leu Leu Glu Pro Ser Pro Ala Asp Gln
        705                 710                 715                 720

Leu Gly Asn Gly His Arg Arg Thr Glu Ser Glu Met Ser Ala Arg Ile
                        725                 730                 735

Ala Lys Met Ser Leu Ser Pro Ser Pro Arg His Glu Asp Gln Leu
                        740                 745                 750

Glu Val Thr Arg Glu Pro Ala Arg Arg Leu Phe Leu Phe Gly Glu Glu
                    755                 760                 765

Pro Ser Lys Leu Asp Gln Asp Val Leu Ala Ala Leu Glu Cys Ala Asp
                    770                 775                 780

Val Asp Pro His Gln Phe Pro Ala Val His Arg Trp Lys Ser Ala Val
        785                 790                 795                 800

Leu Cys Tyr Ser Pro Ser Asp Arg Gln Ser Trp Pro Ser Pro Ala Val
                        805                 810                 815

Lys Gly Arg Phe Lys Ser Gln Leu Pro Asp Leu Ser Gly Pro His Ser
                        820                 825                 830

Tyr Ser Pro Gly Arg Asn Ser Val Ala Gly Ser Asn Pro Ala Lys Pro
                    835                 840                 845

Gly Leu Gly Ser Pro Gly Arg Tyr Ser Pro Val His Gly Ser Gln Leu
                    850                 855                 860

Arg Arg Met Ala Arg Leu Ala Glu Leu Ala Ala Leu
        865                 870                 875
```

<210> SEQ ID NO 3
<211> LENGTH: 254
<212> TYPE: PRT
<213> ORGANISM: Homo sapiens
<400> SEQUENCE: 3

Met Asp Asn Tyr Ala Asp Leu Ser Asp Thr Glu Leu Thr Thr Leu Leu
1               5                   10                  15

Arg Arg Tyr Asn Ile Pro His Gly Pro Val Val Gly Ser Thr Arg Arg
            20                  25                  30

Leu Tyr Glu Lys Lys Ile Phe Glu Tyr Glu Thr Gln Arg Arg Arg Leu
            35                  40                  45

Ser Pro Pro Ser Ser Ser Ala Ser Ser Tyr Ser Phe Ser Asp Leu
50                      55                  60

Asn Ser Thr Arg Gly Asp Ala Asp Met Tyr Asp Leu Pro Lys Lys Glu
65                  70                  75                  80

Asp Ala Leu Leu Tyr Gln Ser Lys Gly Tyr Asn Asp Asp Tyr Tyr Glu
                85                  90                  95

Glu Ser Tyr Phe Thr Thr Arg Thr Tyr Gly Pro Glu Ser Ala Gly
                100                 105                 110

Pro Ser Arg Ala Val Arg Gln Ser Val Thr Ser Phe Pro Asp Ala Asp
            115                 120                 125

Ala Phe His His Gln Val His Asp Asp Leu Leu Ser Ser Ser Glu
130                 135                 140

Glu Glu Cys Lys Asp Arg Glu Arg Pro Met Tyr Gly Arg Asp Ser Ala
145                 150                 155                 160

Tyr Gln Ser Ile Thr His Tyr Arg Pro Val Ser Ala Ser Arg Ser Ser
                165                 170                 175

Leu Asp Leu Ser Tyr Tyr Pro Thr Ser Ser Ser Thr Ser Phe Met Ser
                180                 185                 190

Ser Ser Ser Ser Ser Ser Trp Leu Thr Arg Arg Ala Ile Arg Pro
            195                 200                 205

Glu Asn Arg Ala Pro Gly Ala Gly Leu Gly Gln Asp Arg Gln Val Pro
    210                 215                 220

Leu Trp Gly Gln Leu Leu Phe Leu Val Phe Val Ile Val Leu Phe
225                 230                 235                 240

Phe Ile Tyr His Phe Met Gln Ala Glu Glu Gly Asn Pro Phe
                245                 250

<210> SEQ ID NO 4
<211> LENGTH: 694
<212> TYPE: PRT
<213> ORGANISM: Homo sapiens

<400> SEQUENCE: 4

Met Pro Glu Phe Leu Glu Asp Pro Ser Val Leu Thr Lys Asp Lys Leu
1               5                   10                  15

Lys Ser Glu Leu Val Ala Asn Asn Val Thr Leu Pro Ala Gly Glu Gln
            20                  25                  30

Arg Lys Asp Val Tyr Val Gln Leu Tyr Leu Gln His Leu Thr Ala Arg
            35                  40                  45

Asn Arg Pro Pro Leu Pro Ala Gly Thr Asn Ser Lys Gly Pro Pro Asp
50                  55                  60

Phe Ser Ser Asp Glu Glu Arg Glu Pro Thr Pro Val Leu Gly Ser Gly
65                  70                  75                  80

Ala Ala Ala Ala Gly Arg Ser Arg Ala Ala Val Gly Arg Lys Ala Thr
                85                  90                  95

Lys Lys Thr Asp Lys Pro Arg Gln Glu Asp Lys Asp Asp Leu Asp Val
                100                 105                 110

Thr Glu Leu Thr Asn Glu Asp Leu Leu Asp Gln Leu Val Lys Tyr Gly
            115                 120                 125

```
Val Asn Pro Gly Pro Ile Val Gly Thr Thr Arg Lys Leu Tyr Glu Lys
    130                 135                 140

Lys Leu Leu Lys Leu Arg Glu Gln Gly Thr Glu Ser Arg Ser Ser Thr
145                 150                 155                 160

Pro Leu Pro Thr Ile Ser Ser Ser Ala Glu Asn Thr Arg Gln Asn Gly
                165                 170                 175

Ser Asn Asp Ser Asp Arg Tyr Ser Asp Asn Glu Glu Gly Lys Lys Lys
            180                 185                 190

Glu His Lys Lys Val Lys Ser Thr Arg Asp Ile Val Pro Phe Ser Glu
            195                 200                 205

Leu Gly Thr Thr Pro Ser Gly Gly Phe Phe Gln Gly Ile Ser Phe
            210                 215                 220

Pro Glu Ile Ser Thr Arg Pro Pro Leu Gly Ser Thr Glu Leu Gln Ala
225                 230                 235                 240

Ala Lys Lys Val His Thr Ser Lys Gly Asp Leu Pro Arg Glu Pro Leu
                245                 250                 255

Val Ala Thr Asn Leu Pro Gly Arg Gly Gln Leu Gln Lys Leu Ala Ser
            260                 265                 270

Glu Arg Asn Leu Phe Ile Ser Cys Lys Ser Ser His Asp Arg Cys Leu
            275                 280                 285

Glu Lys Ser Ser Ser Ser Ser Gln Pro Glu His Ser Ala Met Leu
    290                 295                 300

Val Ser Thr Ala Ala Ser Pro Ser Leu Ile Lys Glu Thr Thr Thr Gly
305                 310                 315                 320

Tyr Tyr Lys Asp Ile Val Glu Asn Ile Cys Gly Arg Glu Lys Ser Gly
                325                 330                 335

Ile Gln Pro Leu Cys Pro Glu Arg Ser His Ile Ser Asp Gln Ser Pro
                340                 345                 350

Leu Ser Ser Lys Arg Lys Ala Leu Glu Glu Ser Glu Ser Ser Gln Leu
            355                 360                 365

Ile Ser Pro Pro Leu Ala Gln Ala Ile Arg Asp Tyr Val Asn Ser Leu
            370                 375                 380

Leu Val Gln Gly Gly Val Gly Ser Leu Pro Gly Thr Ser Asn Ser Met
385                 390                 395                 400

Pro Pro Leu Asp Val Glu Asn Ile Gln Lys Arg Ile Asp Gln Ser Lys
                405                 410                 415

Phe Gln Glu Thr Glu Phe Leu Ser Pro Pro Arg Lys Val Pro Arg Leu
            420                 425                 430

Ser Glu Lys Ser Val Glu Glu Arg Asp Ser Gly Ser Phe Val Ala Phe
            435                 440                 445

Gln Asn Ile Pro Gly Ser Glu Leu Met Ser Ser Phe Ala Lys Thr Val
    450                 455                 460

Val Ser His Ser Leu Thr Thr Leu Gly Leu Glu Val Ala Lys Gln Ser
465                 470                 475                 480

Gln His Asp Lys Ile Asp Ala Ser Glu Leu Ser Phe Pro Phe His Glu
                485                 490                 495

Ser Ile Leu Lys Val Ile Glu Glu Trp Gln Gln Val Asp Arg Gln
            500                 505                 510

Leu Pro Ser Leu Ala Cys Lys Tyr Pro Val Ser Ser Arg Glu Ala Thr
            515                 520                 525

Gln Ile Leu Ser Val Pro Lys Val Asp Asp Glu Ile Leu Gly Phe Ile
    530                 535                 540
```

```
Ser Glu Ala Thr Pro Leu Gly Gly Ile Gln Ala Ala Ser Thr Glu Ser
545                 550                 555                 560

Cys Asn Gln Gln Leu Asp Leu Ala Leu Cys Arg Ala Tyr Glu Ala Ala
                565                 570                 575

Ala Ser Ala Leu Gln Ile Ala Thr His Thr Ala Phe Val Ala Lys Ala
            580                 585                 590

Met Gln Ala Asp Ile Ser Gln Ala Ala Gln Ile Leu Ser Ser Asp Pro
        595                 600                 605

Ser Arg Thr His Gln Ala Leu Gly Ile Leu Ser Lys Thr Tyr Asp Ala
    610                 615                 620

Ala Ser Tyr Ile Cys Glu Ala Ala Phe Asp Glu Val Lys Met Ala Ala
625                 630                 635                 640

His Thr Met Gly Asn Ala Thr Val Gly Arg Arg Tyr Leu Trp Leu Lys
                645                 650                 655

Asp Cys Lys Ile Asn Leu Ala Ser Lys Asn Lys Leu Ala Ser Thr Pro
            660                 665                 670

Phe Lys Gly Gly Thr Leu Phe Gly Gly Glu Val Cys Lys Val Ile Lys
        675                 680                 685

Lys Arg Gly Asn Lys His
    690

<210> SEQ ID NO 5
<211> LENGTH: 2628
<212> TYPE: DNA
<213> ORGANISM: Artificial Sequence
<220> FEATURE:
<223> OTHER INFORMATION: Degenerate nucleotide sequence encoding the
      polypeptide of SEQ ID NO:2
<221> NAME/KEY: variation
<222> LOCATION: (1)...(2628)
<223> OTHER INFORMATION: Each N is independently any one of A, T, G or
      C.

<400> SEQUENCE: 5
atgacnatgg aygcnytnyt ngcnmgnytn aarytnytna ayccngayga yytnmgngar      60
garathgtna argcnggnyt naartgyggn ccnathacnw snacnacnmg nttyathtty     120
garaaraary tngcncargc nytnytngar carggnggnm gnytnwsnws nttytaycay     180
caygargcng gngtnacngc nytnwsncar gayccncarm gnathytnaa rccngcngar     240
ggnaayccna cngaycargc nggnttywsn gargaymgng ayttyggnta ywsngtnggn     300
ytnaayccnc cngargarga rgcngtnacn wsnaaracnt gywsngtncc nccnwsngay     360
acngayacnt aymgngcngg ngcnacngcn wsnaargarc cnccnytnta ytayggngtn     420
tgyccngtnt aygargaygt nccngcnmgn aaygarmgna thtaygtnta ygaraayaar     480
aargargcny tncargcngt naaratgath aarggnwsnm gnttyaargc nttywsnacn     540
mgngargayg cngaraartt ygcnmgnggn athtgygayt ayttyccnws nccnwsnaar     600
acnwsnytnc cnytnwsncc ngtnaaracn gcnccnytnt tywsnaayga ymgnytnaar     660
gayggnytnt gyytnwsnga rwsngaracn gtnaayaarg armgngcnaa ywsntayaar     720
aayccnmgna cncargayyt nacngcnaar ytnmgnaarg cngtngaraa rggngargar     780
gayacnttyw sngayytnat htggwsnaay ccnmgntayy tnathggnws nggngayaay     840
ccnacnathg tncargargg ntgymgntay aaygtnatgc aygtngcngc naargaraay     900
cargcnwsna thtgycaryt nacnytngay gtnytngara ayccngaytt yatgmgnytn     960
atgtayccng aygaygayga rgcnatgytn caraarmgna thmgntaygt ngtngayytn    1020
```

-continued tayytnaaya cnccngayaa ratgggntay gayacnccny tncayttygc ntgyaartty 1080
ggnaaygcng aygtngtnaa ygtnytnwsn wsncaycayy tnathgtnaa raaywsnmgn 1140
aayaartayg ayaaracncc ngargaygtn athtgygarm gnwsnaaraa yaarwsngtn 1200
garytnaarg armgnathmg ngartayytn aarggncayt aytaygtncc nytnytnmgn 1260
gcngargara cnwsnwsncc ngtnathggn garytntggw snccngayca racngcngar 1320
gcnwsncayg tnwsnmgnta yggnggnwsn ccnmgngayc cngtnytnac nytnmgngcn 1380
ttygcnggnc cnytnwsncc ngcnaargcn gargayttym gnaarytntg gaaracnccn 1440
ccnmgngara argcnggntt yytncaycay gtnaaraarw sngayccnga rmgnggntty 1500
garmgngtng gnmgngaryt ngcncaygar ytnggntayc cntgggtnga rtaytgggar 1560
ttyytnggnt gyttygtnga yytnwsnwsn cargarggny tncarmgnyt ngargartay 1620
ytnacncarc argarathgg naaraargcn carcargara cnggngarmg ngargcnwsn 1680
tgymgngaya argcnacnac nwsnggnwsn aaywsnathw sngtnmgngc nttyytngay 1740
gargaygaya tgwsnytnga rgarathaar aaymgncara aygcngcnmg naayaaywsn 1800
ccnccnacng tnggngcntt yggncayacn mgntgywsng cnttyccnyt ngarcargar 1860
gcngayytna thgargcngc ngarccnggn ggnccncayw snwsnmgnaa yggnytntgy 1920
cayccnytna aycaywsnmg nacnytngcn ggnaarmgnc cnaargcncc ncayggngar 1980
gargcncayy tnccnccngt nwsngayytn acngtngart tygayaaryt naayytncar 2040
aayathggnm gnwsngtnws naaracnccn gaygarwsna cnaaracnaa rgaycarath 2100
ytnacnwsnm gnathaaygc ngtngarmgn gayytnytng arccnwsncc ngcngaycar 2160
ytnggnaayg gncaymgnmg nacngarwsn garatgwsng cnmgnathgc naaratgwsn 2220
ytnwsnccnw snwsnccnmg ncaygargay carytngarg tnacnmgnga rccngcnmgn 2280
mgnytnttyy tnttyggnga rgarccnwsn aarytngayc argaygtnyt ngcngcnytn 2340
gartgygcng aygtngaycc ncaycartty ccngcngtnc aymgntggaa rwsngcngtn 2400
ytntgytayw snccnwsnga ymgncarwsn tggccnwsnc cngcngtnaa rggnmgntty 2460
aarwsncary tnccngayyt nwsnggnccn caywsntayw snccnggnmg naaywsngtn 2520
gcnggnwsna ayccngcnaa rccnggnytn ggnwsnccng gnmgntayws nccngtncay 2580
ggnwsncary tnmgnmgnat ggcnmgnytn gcngarytng cngcnytn 2628

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide ZC15487

<400> SEQUENCE: 6
ggacccatta catcaact 18

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide ZC15486

<400> SEQUENCE: 7
cctccttgct ccagtaaa 18

<210> SEQ ID NO 8
<211> LENGTH: 218
<212> TYPE: DNA
<213> ORGANISM: Artificial Sequence
<220> FEATURE:
<223> OTHER INFORMATION: Northern Blot probe

<400> SEQUENCE: 8

```
ctcaggcttt actggagcaa ggaggaaggc tgtcttcttt ctaccaccat gaggcaggtg      60
tcacagctct cagccaggac ccacaaagga ttttgaagcc agctgaaggg aacccaactg     120
atcaggctgg tttttctgaa gacagagatt ttggttacag tgtgggcctg aatcctccag     180
aggaggaagc tgtgacatcc aagacctgct cggtgccc                             218
```

<210> SEQ ID NO 9
<211> LENGTH: 18
<212> TYPE: DNA
<213> ORGANISM: Artificial Sequence
<220> FEATURE:
<223> OTHER INFORMATION: ZC694

<400> SEQUENCE: 9

```
taatacgact cactatag                                                    18
```

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide ZC976

<400> SEQUENCE: 10

```
cgttgtaaaa cgacggcc                                                    18
```

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide ZC15976

<400> SEQUENCE: 11

```
cagctctgta ggtgtcggtg tc                                               22
```

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide ZC15485

<400> SEQUENCE: 12

```
caccgacacc tacagagc                                                    18
```

<210> SEQ ID NO 13
<211> LENGTH: 25
<212> TYPE: DNA
<213> ORGANISM: Artificial Sequence
<220> FEATURE:
<223> OTHER INFORMATION: ZC15526

<400> SEQUENCE: 13

```
tgctccagta aagcctgagc caatt                                            25
```

<210> SEQ ID NO 14

```
<211> LENGTH: 17
<212> TYPE: DNA
<213> ORGANISM: Artificial Sequence
<220> FEATURE:
<223> OTHER INFORMATION: Oligonucleotide ZC447

<400> SEQUENCE: 14
taacaatttc acacagg                                                  17

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide ZC15620

<400> SEQUENCE: 15
acagagctgg agcgactgcg                                               20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide ZC15823

<400> SEQUENCE: 16
tctctttggc agcaacatgc                                               20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide ZC16162

<400> SEQUENCE: 17
gtgcaggtac aacgtgatgc                                               20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide ZC16035

<400> SEQUENCE: 18
ctgacttcat gaggctgatg                                               20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide ZC16249

<400> SEQUENCE: 19
cagggtacat cagcctcatg                                               20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide ZC16164

<400> SEQUENCE: 20
```

```
tctgtcttcc caggaaggcc                                          20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide ZC16163

<400> SEQUENCE: 21
ggaattgctg ccagacgtgg                                          20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide ZC16165

<400> SEQUENCE: 22
agagccttct cccgcagacc                                          20

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide 16037

<400> SEQUENCE: 23
ggctgctggg actcaaggac                                          20

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide AP1

<400> SEQUENCE: 24
ccatcctaat acgactcact atagggc                                  27

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide ZC15527

<400> SEQUENCE: 25
ctcatggtgg tagaaagaag acagc                                    25

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide ZC695

<400> SEQUENCE: 26
gatttaggtg acactatag                                           19

<210> SEQ ID NO 27
<211> LENGTH: 424
<212> TYPE: DNA
```

-continued

```
<213> ORGANISM: Artificial Sequence
<220> FEATURE:
<223> OTHER INFORMATION: EST934031
<221> NAME/KEY: variation
<222> LOCATION: (1)...(424)
<223> OTHER INFORMATION: Each N is independently A, T, G, or C

<400> SEQUENCE: 27
gctcgattga aacttctgaa tccagatgac cttagagaag aaatcgtcaa agccggattg      60
aaatgtggac ccattacatc aactacaagg ttcattttg agaaaaatt ggctcaggct      120 ttactggagc aaggaggaag gctgtcttct ttctaccacc atgaggcagg tgtcacagct      180
ctcagccagg acccacaaag gattttgaag ccagctgaag ggacccaac tgatcaggct      240 ggttttctg aagacagaga ttttggttac agtgtgggcc tgaatcctcc agaggaggaa      300
gctgtgacat ccaagacctg ctcggtgccc cctagtgaca ccgacaccta cagagctgga      360
gcgactgcgt ctataggagc cgcccctgt actatgnggg tgtgtccagt tgtatgagga      420
cgtc                                                                 424

<210> SEQ ID NO 28
<211> LENGTH: 24
<212> TYPE: DNA
<213> ORGANISM: Artificial Sequence
<220> FEATURE:
<223> OTHER INFORMATION: Oligonucleotide ZC15521

<400> SEQUENCE: 28
gggcaccgag caggtcttgg atgt                                            24

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide ZC15525

<400> SEQUENCE: 29
ctcaggcttt actggagcaa ggagg                                           25

<210> SEQ ID NO 30
<211> LENGTH: 454
<212> TYPE: PRT
<213> ORGANISM: Homo sapiens

<400> SEQUENCE: 30

Met Pro Glu Phe Leu Glu Asp Pro Ser Val Leu Thr Lys Asp Lys Leu
 1               5                  10                  15

Lys Ser Glu Leu Val Ala Asn Asn Val Thr Leu Pro Ala Gly Glu Gln
                20                  25                  30

Arg Lys Asp Val Tyr Val Gln Leu Tyr Leu Gln His Leu Thr Ala Arg
            35                  40                  45

Asn Arg Pro Pro Leu Pro Ala Gly Thr Asn Ser Lys Gly Pro Pro Asp
        50                  55                  60

Phe Ser Ser Asp Glu Glu Arg Glu Pro Thr Pro Val Leu Gly Ser Gly
65                  70                  75                  80

Ala Ala Ala Ala Gly Arg Ser Arg Ala Ala Val Gly Arg Lys Ala Thr
                85                  90                  95

Lys Lys Thr Asp Lys Pro Arg Gln Glu Asp Lys Asp Asp Leu Asp Val
               100                 105                 110

Thr Glu Leu Thr Asn Glu Asp Leu Leu Asp Gln Leu Val Lys Tyr Gly
```

-continued

```
                115                 120                 125
Val Asn Pro Gly Pro Ile Val Gly Thr Thr Arg Lys Leu Tyr Glu Lys
    130                 135                 140

Lys Leu Lys Leu Arg Glu Gln Gly Thr Glu Ser Arg Ser Ser Thr
145                 150                 155                 160

Pro Leu Pro Thr Ile Ser Ser Ala Glu Asn Thr Arg Gln Asn Gly
                165                 170                 175

Ser Asn Asp Ser Asp Arg Tyr Ser Asp Asn Glu Glu Asp Ser Lys Ile
            180                 185                 190

Glu Leu Lys Leu Glu Lys Arg Glu Pro Leu Lys Gly Arg Ala Lys Thr
        195                 200                 205

Pro Val Thr Leu Lys Gln Arg Arg Val Glu His Asn Gln Ser Tyr Ser
    210                 215                 220

Gln Ala Gly Ile Thr Glu Thr Glu Trp Thr Ser Gly Ser Ser Lys Gly
225                 230                 235                 240

Gly Pro Leu Gln Ala Leu Thr Arg Glu Ser Thr Arg Gly Ser Arg Arg
                245                 250                 255

Thr Pro Arg Lys Arg Val Glu Thr Ser Glu His Phe Arg Ile Asp Gly
            260                 265                 270

Pro Val Ile Ser Glu Ser Thr Pro Ile Ala Glu Thr Ile Met Ala Ser
        275                 280                 285

Ser Asn Glu Ser Leu Val Val Asn Arg Val Thr Gly Asn Phe Lys His
    290                 295                 300

Ala Ser Pro Ile Leu Pro Ile Thr Glu Phe Ser Asp Ile Pro Arg Arg
305                 310                 315                 320

Ala Pro Lys Lys Pro Leu Thr Arg Ala Glu Val Gly Glu Lys Thr Glu
                325                 330                 335

Glu Arg Arg Val Glu Arg Asp Ile Leu Lys Glu Met Phe Pro Tyr Glu
            340                 345                 350

Ala Ser Thr Pro Thr Gly Ile Ser Ala Ser Cys Arg Arg Pro Ile Lys
        355                 360                 365

Gly Ala Ala Gly Arg Pro Leu Glu Leu Ser Asp Phe Arg Met Glu Glu
    370                 375                 380

Ser Phe Ser Ser Lys Tyr Val Pro Lys Tyr Val Pro Leu Ala Asp Val
385                 390                 395                 400

Lys Ser Glu Lys Thr Lys Lys Gly Arg Ser Ile Pro Val Trp Ile Lys
                405                 410                 415

Ile Leu Leu Phe Val Val Val Ala Val Phe Leu Phe Leu Val Tyr Gln
            420                 425                 430

Ala Met Glu Thr Asn Gln Val Asn Pro Phe Ser Asn Phe Leu His Val
        435                 440                 445

Asp Pro Arg Lys Ser Asn
    450

<210> SEQ ID NO 31
<211> LENGTH: 345
<212> TYPE: PRT
<213> ORGANISM: Homo sapiens

<400> SEQUENCE: 31

Met Pro Glu Phe Leu Glu Asp Pro Ser Val Leu Thr Lys Asp Lys Leu
1               5                   10                  15

Lys Ser Glu Leu Val Ala Asn Asn Val Thr Leu Pro Ala Gly Glu Gln
            20                  25                  30
```

Arg Lys Asp Val Tyr Val Gln Leu Tyr Leu Gln His Leu Thr Ala Arg
            35                  40                  45

Asn Arg Pro Leu Pro Ala Gly Thr Asn Ser Lys Gly Pro Pro Asp
 50                  55                  60

Phe Ser Ser Asp Glu Glu Arg Glu Pro Thr Pro Val Leu Gly Ser Gly
 65                  70                  75                  80

Ala Ala Ala Ala Gly Arg Ser Arg Ala Ala Val Gly Arg Lys Ala Thr
                 85                  90                  95

Lys Lys Thr Asp Lys Pro Arg Gln Glu Asp Lys Asp Asp Leu Asp Val
                100                 105                 110

Thr Glu Leu Thr Asn Glu Asp Leu Leu Asp Gln Leu Val Lys Tyr Gly
                115                 120                 125

Val Asn Pro Gly Pro Ile Val Gly Thr Thr Arg Lys Leu Tyr Glu Lys
    130                 135                 140

Lys Leu Leu Lys Leu Arg Glu Gln Gly Thr Glu Ser Arg Ser Ser Thr
145                 150                 155                 160

Pro Leu Pro Thr Ile Ser Ser Ser Ala Glu Asn Thr Arg Gln Asn Gly
                165                 170                 175

Ser Asn Asp Ser Asp Arg Tyr Ser Asp Asn Glu Glu Asp Ser Lys Ile
                180                 185                 190

Glu Leu Lys Leu Glu Lys Arg Glu Pro Leu Lys Gly Arg Ala Lys Thr
                195                 200                 205

Pro Val Thr Leu Lys Gln Arg Arg Val Glu His Asn Gln Val Gly Glu
    210                 215                 220

Lys Thr Glu Glu Arg Arg Val Glu Arg Asp Ile Leu Lys Glu Met Phe
225                 230                 235                 240

Pro Tyr Glu Ala Ser Thr Pro Thr Gly Ile Ser Ala Ser Cys Arg Arg
                245                 250                 255

Pro Ile Lys Gly Ala Ala Gly Arg Pro Leu Glu Leu Ser Asp Phe Arg
                260                 265                 270

Met Glu Glu Ser Phe Ser Ser Lys Tyr Val Pro Lys Tyr Val Pro Leu
                275                 280                 285

Ala Asp Val Lys Ser Glu Lys Thr Lys Lys Gly Arg Ser Ile Pro Val
    290                 295                 300

Trp Ile Lys Ile Leu Leu Phe Val Val Val Ala Val Phe Leu Phe Leu
305                 310                 315                 320

Val Tyr Gln Ala Met Glu Thr Asn Gln Val Asn Pro Phe Ser Asn Phe
                325                 330                 335

Leu His Val Asp Pro Arg Lys Ser Asn
                340                 345

<210> SEQ ID NO 32
<211> LENGTH: 23
<212> TYPE: DNA
<213> ORGANISM: Artificial Sequence
<220> FEATURE:
<223> OTHER INFORMATION: Oligonucleotide AP2

<400> SEQUENCE: 32
actcactata gggctcgagc ggc                                                  23

<210> SEQ ID NO 33
<211> LENGTH: 12
<212> TYPE: DNA
<213> ORGANISM: Artificial Sequence
<220> FEATURE:
<223> OTHER INFORMATION: Contig sequence

```
<400> SEQUENCE: 33
atggcttagc tt                                                          12

<210> SEQ ID NO 34
<211> LENGTH: 12
<212> TYPE: DNA
<213> ORGANISM: Artificial Sequence
<220> FEATURE:
<223> OTHER INFORMATION: Contig sequence

<400> SEQUENCE: 34
tagcttgagt ct                                                          12

<210> SEQ ID NO 35
<211> LENGTH: 12
<212> TYPE: DNA
<213> ORGANISM: Artificial Sequence
<220> FEATURE:
<223> OTHER INFORMATION: Contig sequence

<400> SEQUENCE: 35
gtcgactacc ga                                                          12
```

SOLUBLE PROTEIN ZTMPO-1

This application claims the benefit of U.S. Provisional Application No. 60/082,513, filed Apr. 21, 1998.

BACKGROUND OF THE INVENTION

There is a growing family of proteins which share regions of sequence homology and localization to the nucleus. These proteins include the thymopoietins, (Zevin-Sonkin et al., *Immuno. Letts.* 31:301–10, 1992; Harris et al., *Proc. Natl. Acad. Sci. USA* 91:6283–87, 1994; Harris et al., *Genomics* 28:198–205, 1995; Berger et al., *Genome Res.* 6:361–70, 1996 and Ishijima et al., *Biochem. Biophys. Res. Comm.* 226:431–8, 1996), lamina associated proteins, (Senior and Gerace, *J. Cell Biol.* 107:2029–36, 1988; Worman et al., *J. Cell Biol.* 111:1535–42, 1990; Wozniak and Blobel *J. Cell Biol.* 119:1441–9, 1992; Foisner and Gerace, *Cell* 73:1267–79, 1993; Ye and Worman, *J. Biol. Chem.* 269:11306–11, 1994 and Furukawa et al., *EMBO J.* 14:1626–36, 1995) and emerin (Bione et al., *Nat. Genet.* 8:323–7, 1994; Manilal et al., *Hum. Mol. Gen.* 5:801–8, 1996 and Small et al., *Mamm. Genom.* 8:337–41, 1997).

Emerin is a nuclear membrane protein responsible for the X-linked recessive disorder Emery-Dreifuss muscular dystrophy. Mouse, rat and human emerin sequences have been reported (Bione et al., *Nat. Genet.* 8:323–7, 1994; Manila et al., *Hum. Mol. Genet.* 5:801–8, 1996 and Small et al., *Mammal. Genom.* 8:337–41, 1997). The mouse, rat and human emerin share 73–95% nucleotide and amino acid identity. All share some structural homology with the thymopoietins and LAP2, in particular within portions of the conserved N-terminal region and the hydrophobic putative transmembrane domain of thymopoietin. Like the thymopoietins and LAP2, emerin is ubiquitous expressed and it is predicted that emerin has the same inner nuclear membrane organization as do thymopoietin and LAP2 (Manilal et al., ibid.). Antisera raised against emerin peptides localized expression of the protein to the nuclear membranes of normal skeletal and cardiac muscle cells, but found it to be absent in those cells of patients with muscular dystrophy. It is unclear how a deficiency of a nuclear protein results in the disease (Nagano et al., *Nat. Genet.* 12:254–9, 1996 and Small et al., ibid.).

The present invention provides associated polypeptides for these and other uses that should be apparent to those skilled in the art from the teachings herein.

SUMMARY OF THE INVENTION

Within one aspect the invention provides an isolated polypeptide comprising a sequence of amino acid residues that is at least 80% identical in amino acid sequence to residues 1 through 876 of SEQ ID NO:2. Within one embodiment the sequence of amino acid residues is at least 90% identical. Within another embodiment any differences between said polypeptide and residues 1 through 876 of SEQ ID NO:2 are due to conservative amino acid substitutions. Within another embodiment the polypeptide specifically binds with an antibody that specifically binds with a polypeptide consisting of the amino acid sequence of SEQ ID NO:2. Within a further embodiment the polypeptide is covalently linked to a moiety selected from the group consisting of affinity tags, radionucleotides, enzymes and fluorophores. Within a related embodiment the moiety is an affinity tag selected from the group consisting of polyhistidine, FLAG, Glu-Glu, glutathione S transferase and an immunoglobulin heavy chain constant region.

Also provided is an isolated polypeptide comprising the amino acid sequence of SEQ ID NO:2.

Within another aspect the invention provides a fusion protein consisting essentially of a first portion and a second portion joined by a peptide bond, said first portion consisting of a polypeptide comprising a sequence of amino acid residues that is at least 80% identical in amino acid sequence to residues 1 through 876 of SEQ ID NO:2; and said second portion comprising another polypeptide.

Within yet another aspect the invention provides a pharmaceutical composition comprising a polypeptide as described above, in combination with a pharmaceutically acceptable vehicle.

Within still another aspect is provided an antibody or antibody fragment that specifically binds to a polypeptide as described above. Within one embodiment the antibody is selected from the group consisting of: a) polyclonal antibody; b) murine monoclonal antibody; c) humanized antibody derived from b); and d) human monoclonal antibody. Within another embodiment the antibody fragment is selected from the group consisting of F(ab'), F(ab), Fab', Fab, Fv, scFv, and minimal recognition unit. Within still another embodiment is provided an anti-idiotype antibody that specifically binds to the antibody described above.

Also provided is a binding protein that specifically binds to an epitope of a polypeptide as described above.

Within another aspect of the invention is provided an isolated polynucleotide selected from the group consisting of: a) a polynucleotide encoding a polypeptide comprising a sequence of amino acid residues that is at least 80% identical in amino acid sequence to residues 1 through 876 of SEQ ID NO:2; b) a polynucleotide comprising the nucleotide sequence of SEQ ID NO:5; c) a polynucleotide that remains hybridized following stringent wash conditions to a polynucleotide consisting of the nucleotide sequence of SEQ ID NO:1, or the complement of SEQ ID NO:1. Within one embodiment the sequence of amino acid residues is at least 90% identical. Within another embodiment any difference between the amino acid sequence encoded by the polynucleotide and the corresponding amino acid sequence of SEQ ID NO:2 is due to a conservative amino acid substitution. Within yet another embodiment the polynucleotide comprises nucleotide 127 to nucleotide 2754 of SEQ ID NO:1. Within still another embodiment the polynucleotide is DNA.

Within another aspect the invention provides an expression vector comprising the following operably linked elements: a transcription promoter; a DNA segment consisting of a polynucleotide as described above; and a transcriptional terminator. Within one embodiment the sequence of amino acid residues is at least 90% identical. Within another embodiment any difference between the amino acid sequence encoded by the polynucleotide and the corresponding amino acid sequence of SEQ ID NO:2 is due to a conservative amino acid substitution. Within another embodiment the DNA segment encodes a polypeptide covalently linked to an affinity tag selected from the group consisting of polyhistidine, Glu-Glu, glutathione S transferase and an immunoglobulin heavy chain constant region. Within yet another embodiment the expression vector further comprises a secretory signal sequence operably linked to said DNA segment.

Also provided is a cultured cell into which has been introduced an expression vector as described above, wherein the cell expresses the polypeptide encoded by the DNA segment.

Within a further aspect the invention provide a method of producing a ZTMPO-1 polypeptide comprising: culturing a cell into which has been introduced an expression vector as described above, whereby the cell expresses the polypeptide encoded by the DNA segment; and recovering the expressed polypeptide.

Also provided by the invention is a method for detecting a genetic abnormality in a patient, comprising: obtaining a genetic sample from a patient; incubating the genetic sample with a polynucleotide comprising at least 14 contiguous nucleotides of SEQ ID NO:1 or the complement of SEQ ID NO:1, under conditions wherein said polynucleotide will hybridize to complementary polynucleotide sequence, to produce a first reaction product; comparing said first reaction product to a control reaction product, wherein a difference between said first reaction product and said control reaction product is indicative of a genetic abnormality in the patient.

These and other aspects of the invention will become evident upon reference to the following detailed description of the invention and attached drawing.

BRIEF DESCRIPTION OF THE DRAWINGS

The figure shows a multiple amino acid sequence alignment for ZTMPO-1 (SEQ ID NO:2), human emerin (EMD$_{13}$HU) Bione et al., *Nat. Genet.* 8:323–27, 1994 (SEQ ID NO:3), human thymopoietin α (PIR_A5) Harris et al., *Proc. Natl. Acad. Sci. USA* 91: 6283–7, 1994 (SEQ ID NO:4), human thymopoietin β (PIR_B5) Harris et al., ibid. (SEQ ID NO:30) and human thymopoietin γ (PIR_C5) Harris et al., ibid. (SEQ ID NO:31).

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag, substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or alone a partial stretch of the polynucleotide. For example, representative contigs to the polynucleotide sequence 5'-ATGGCTTAGCTT-3' (SEQ ID NO:33) are 5'-TAGCTTgagtct-3' (SEQ ID NO:34) and 3'-gtcgacTACCGA-5' (SEQ ID NO:35).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, OR, and Amersham Corp., Arlington Heights, Ill, using techniques that are well known in the art. Examples of ZTMPO-1 probes and primers include, but are not limited to, the sequences disclosed herein as SEQ ID NOs:6–29.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel protein having regions of homology to members of the thymopoietin-emerin family of nuclear membrane proteins. This protein has been designated "ZTMPO-1". The human ZTMPO-1 nucleotide sequence is represented in SEQ ID NO:1 and the deduced amino acid sequence in SEQ ID NO:2. The ZTMPO-1 proteins and polypeptides encoded by polynucleotides of the present invention were initially identified by querying an EST (Expressed Sequence Tag) database for sequences homologous to conserved motifs within the thymopoietin family. ZTMPO-1 as represented in SEQ ID NO:1 is a 2,754 bp polynucleotide which has an open reading frame encoding an 876 amino acid residue protein. Sequence analysis of the deduced amino acid sequence as represented in SEQ ID NO:2 does not indicate the presence of a secretion signal sequence or transmembrane domain. There is a putative ankyrin-like region, amino acid residues 333–385 of SEQ ID NO:2, having an ankyrin repeat (residues 347–379 of SEQ ID NO:2) which may indicate that ZTMPO-1 is retained in the plasma membrane. Ankyrin repeats have been described as a 33 amino acid motif, usually found in tandem arrays of four to seven copies, that mediate protein interactions (Michaely and Bennett, *J. Biol. Chem.* 268:22703–9, 1993). Ankyrin repeats have been reported in numerous proteins in species from bacteria to man (Sentenac et al., *Science.* 256:663–5, 1992; Zhang et al., *Plant Cell* 4:1575–88, 1992; Gustine et al., *Plant Physiol.* 108:1748, 1995; Andrews and Herskowitz, *Nature* 342:830–3, 1989; Warton et al., *Cell* 43:567–81, 1995 and Yochem and Greenwald, *Cell* 58:53–63, 1989. Ankyrin repeats have been proposed as a generalized protein binding motif, one function of ankyrin repeats is to serve as adaptors, associating with the spectrin-based cytoplasmic skeleton and membrane proteins. Ankyrin is used as a membrane attachment site in neurons and may provide a transport mechanism through secretory vesicles.

At the C-terminal end of ZTMPO-1 is a calcium binding protein-like region having two potential calcium binding sites (residues 678–692 and residues 719–731 of SEQ ID NO:2) similar to that seen in the sea urchin calcium binding protein LPS1-beta (Xiang et al., *J. Biol. Chem.* 16:10524–33, 1991).

The ZTMPO-1 polynucleotide of SEQ ID NO:1 encodes an 876 amino acid residue protein which is much larger than other members of the thymopoietin/emerin family. Human thymopoietin α is a 693 amino acid residue protein, human emerin is a 254 amino acid residue protein and rat LAP2 is a 452 amino acid residue protein.

Like emerin, the amino acid sequence of ZTMPO-1 does not contain the 42 amino acid thymopoietin peptide originally identified by Goldstein (*Nature* 247:11–14, 1974) but shares discrete regions of homology with the human thymopoietins α, β and γ (Harris et al., ibid., Genbank Accession Nos. α (U09086), β (U09087) and γ (U09088)) and the mouse thymopoietins α, β, γ, ε, δ, and ζ (Berger et al., ibid., Genbank Accession Nos. α (U39078), β U39074, γ (U39077), ε (U39074), δ (U39076) and ζ (U39073)). In particular, over the region defined by amino acid residues 13 to 44 of SEQ ID NO:2, ZTMPO-1 shares 50% amino acid identity with the corresponding regions of the mouse and human thymopoietins and 30% with human emerin. In particular, the region defined by amino acid residues 30–44 of SEQ ID NO:2 is highly conserved between the proteins, see Figure.

As would be expected, ZTMPO-1 also shares discrete regions of homology with rat lamina associated protein 2, LAP2, (Furukawa et al., ibid., Genbank Accession No. U18314). These regions correspond to many of the same regions with which ZTMPO-1 shares identity with the thymopoietins. ZTMPO-1 and rat LAP2 share 70% amino acid identity over the region corresponding to amino acid residues 13 to 44 of SEQ ID NO:2.

ZTMPO-1 also shares a limited degree of homology to regions of the yeast transcription factor IIF alpha subunit over the region corresponding to amino acid residues 86 to 160 and amino acid residues 205 to 260 of SEQ ID NO:2.

Additionally, ZTMPO-2 shares 27% amino acid identity with Trypanosoma brucei ribonuclease H1 Hesslein and Campbell, *Mol. Biochem. Parasitol.* 86:121–6, 1997, Genbank Accession No. U74470) over the region corresponding to amino acid residues 156 to 203 of SEQ ID NO:2. This homology, along with that shared with LAP2, as well as the possible ankyrin repeat, suggests the possibility that ZTMPO-1 possesses chromatin or DNA binding properties.

Those skilled in the art will recognize that these domain boundaries are approximate, and are based on alignments with known proteins and predictions of protein folding.

Northern blot analysis of various human tissues was performed using a 218 bp human DNA probe (SEQ ID NO:8). A 3.2 and a 5 kb transcript corresponding to ZTMPO-1 were ubiquitously expressed with the highest level being in testis tissue. Similar ubiquitous expression patterns were also reported for the thymopoietins and emerin (Harris et al., ibid. and Small et al., ibid.).

Chromosomal localization results show that ZTMPO-1 maps 636.18 cR__3000 from the top of the human chromosome 12 linkage group on the WICGR radiation hybrid map. The proximal framework marker was D12S367. The use of surrounding markers positions ZTMPO-1 in the 12q24.33 region on the integrated LDB chromosome 12 map. Among the genes mapping around this region are insulin-like growth factor 1 which is involved in growth and development; melanin concentrating hormone, a neuropeptide associated with goal-associated behaviors and general arousal (Nahon et al., *Genomics* 12: 846–8, 1992); spinal muscular atrophy a nonprogressive muscular atrophy involving mainly the lower extremities (van Ravenswaaij, et al., *Am. J. Hum. Genet.* 61 (suppl.): A299, 1997); spinal muscular atrophy 4 (Timmerman, et al., *Hum. Molec. Genet.* 5: 1065–9, 1996) and myosin regulatory light chain which is involved in regulation of myosin ATPase activity in smooth muscle (Macera, et al., *Genomics* 13: 829–31, 1992). Thymopoietin maps to chromosome 12q22 (Harris et al., ibid.).

The nucleotide sequences encoding regions of conserved amino acid residues between ZTMPO-1 and nuclear proteins such as the thymopoietins, LAP2 and emerin, for example, the region between nucleotides 163 and 258 of SEQ ID NO:1, in particular the region between nucleotides 214 and 258 of SEQ ID NO:1, can be used as a tool to identify new family members. For instance, reverse transcription-polymerase chain reaction (RT-PCR) can be used to amplify sequences encoding these conserved regions from RNA obtained from a variety of tissue sources or cell lines. In particular, highly degenerate primers designed from the ZTMPO-1 sequences are useful for this purpose.

The present invention also provides polynucleotide molecules, including DNA and RNA molecules, that encode the ZTMPO-1 polypeptides disclosed herein. Those skilled in the art will readily recognize that, in view of the degeneracy of the genetic code, considerable sequence variation is possible among these polynucleotide molecules. SEQ ID NO:5 is a degenerate DNA sequence that encompasses all DNAs that encode the ZTMPO-1 polypeptide of SEQ ID NO:2. Those skilled in the art will recognize that the degenerate sequence of SEQ ID NO:5 also provides all RNA sequences encoding SEQ ID NO:2 by substituting U (uracil) for T (thymine). Thus, ZTMPO-1 polypeptide-encoding polynucleotides comprising nucleotide 1 to nucleotide 2628 of SEQ ID NO:5 and their RNA equivalents are contemplated by the present invention. Table 1 sets forth the one-letter codes used within SEQ ID NO:5 to denote degenerate nucleotide positions. "Resolutions" are the nucleotides denoted by a code letter. "Nucleotide Complement" indicates the code for the complementary nucleotide(s). For example, the code Y denotes either C (cytosine) or T, and its complement R denotes A (adenosine) or G (guanine), A being complementary to T, and G being complementary to C.

TABLE 1

| Base Code | Resolutions | Base Code | Nucleotide Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:5, encompassing all possible codons for a given amino acid, are set forth in Table 2.

TABLE 2

| Three Letter Code | One Letter Code | Synonymous Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.*, 8:1893–912, 1980; Haas, et al. *Curr. Biol.*, 6:315–24, 1996; Wain-Hobson, et al., Gene, 13:355–64, 1981; Grosjean and Fiers, *Gene*, 18:199–209, 1982; Holm, *Nuc. Acids Res.*, 14:3075–87, 1986; Ikemura, *J. Mol. Biol.*, 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:5 serves as a template for optimizing expression of polynucleotides in various cell types and species commonly used in the art and disclosed herein. Sequences containing preferential codons can be tested and optimized for expression in various species, and tested for functionality as disclosed herein.

The present invention also provides polypeptide fragments or peptides comprising an epitope-bearing portion of an ZTMPO-1 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat. Acad. Sci. USA* 81:3998, 1983).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660, 1983). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2. Such epitope-bearing peptides and polypeptides can be produced by fragmenting a ZTMPO-1 polypeptide, or by chemical peptide synthesis, as escribed herein. Moreover, epitopes can be selected by hage display of random peptide libraries (see, for example, Lane and Stephen, *Curr. Opin. Immunol.* 5:268, 1993, and Cortese et al., *Curr. Opin. Biotechnol.* 7:616, 1996). Standard methods for identifying epitopes and producing antibodies from small peptides that comprise an epitope are described, for example, by Mole, "Epitope Mapping," in *Methods in Molecular Biology*, Vol10, Manson (ed.), pages 105–116 (The Humana Press, Inc. 1992), Price, "Production and Characterization of Synthetic Peptide-Derived Antibodies," in *Monoclonal Antibodies: Production, Engineering and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

Potential antigenic sites in ZTMPO-1 can be identified using the Jameson-Wolf method (Jameson and Wolf, *CABIOS* 4:181, 1988), as implemented by the PROTEAN program (version 3.14) of LASERGENE (DNASTAR; Madison, WI). The Jameson-Wolf method predicts potential antigenic determinants by combining six major subroutines for protein structural prediction. Briefly, the Hopp-Woods method (Hopp et al., *Proc. Nat. Acad. Sci. USA* 78:3824, 1981), is first used to identify amino acid sequences representing areas of greatest local hydrophilicity (parameter: seven residues averaged). In the second step, Emini's method (Emini et al., *J. Virology* 55:836, 1985), is used to calculate surface probabilities (parameter: surface decision threshold (0.6)=1). Third, the Karplus-Schultz method, (Karplus and Schultz, *Naturwissenschaften* 72:212, 1985), is used to predict backbone chain flexibility (parameter: flexibility threshold (0.2)=1). In the fourth and fifth steps of the analysis, secondary structure predictions are applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549–586 (Plenum Press 1990), and Garnier-Robson, Garnier et al., *J. Mol. Biol.* 120:97, 1978 (Chou-Fasman parameters: conformation table=64 proteins; a region threshold=103; b region threshold=105; Garnier-Robson parameters: a and b decision constants=0). In the sixth subroutine, flexibility parameters and hydropathy/solvent accessibility factors are combined to determine a surface contour value, designated as the "antigenic index." Finally, a peak broadening function is applied to the antigenic index, which broadens major surface peaks by adding 20, 40, 60, or 80% of the respective peak value to account for additional free energy derived from the mobility of surface regions relative to interior regions.

Regardless of the particular nucleotide sequence of a variant ZTMPO-1 gene, the gene encodes a polypeptide that is characterized by its glycoprotein synthesis or cell-cell interaction activity, or by the ability to bind specifically to an anti-ZTMPO-1 antibody. More specifically, variant ZTMPO-1 genes encode polypeptides which exhibit at least 50%, and preferably, greater than 70, 80, or 90%, of the activity of polypeptide encoded by the human ZTMPO-1 gene described herein.

For any ZTMPO-1 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise ZTMPO-1 variants based upon the nucleotide and amino acid sequences described herein. Accordingly, the present invention includes a computer-readable medium encoded with a data structure that provides at least one of the following sequences: SEQ ID NO:1, SEQ ID NO:2 or SEQ ID NO:5. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

Within preferred embodiments of the invention, the isolated polynucleotides can hybridize under stringent conditions to polynucleotides having the nucleotide sequence of SEQ ID NO:1 or to nucleic acid molecules having a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6xSSC and 0–50% formamide. A higher degree of stringency can be achieved at temperatures of from 40–70° C. with a hybridization buffer having up to 4xSSC and from 0–50% formamide. Highly stringent conditions typically encompass temperatures of 42–70° C. with a hybridization buffer having up to 1xSSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software, such as OLIGO 6.0 (LSR; Long Lake, MN) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are typically allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1xSSC: 0.15 M sodium chloride, 15 mM sodium citrate) or SSPE (1xSSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM–1 M $Na^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a polynucleotide encoding a variant ZTMPO-1 polypeptide can be hybridized with a polynucleotide having the nucleotide sequence of SEQ ID NO:1 (or its complement) at 42° C. overnight in a solution comprising 50% formamide, 5xSSC (1xSSC: 0.15 M sodium chloride and 15 mM sodium citrate), 50 mM sodium phosphate (pH 7.6), 5xDenhardt's solution (100xDenhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher or lower temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5x–2xSSC with 0.1% sodium dodecyl sulfate (SDS) at 55–65° C. That is, nucleic acid molecules encoding a variant ZTMPO-1 polypeptide hybridize with a nucleic acid molecule having the nucleotide sequence of SEQ ID NO:1 (or its complement) under stringent washing conditions, in which the wash stringency is equivalent to 0.5x–2xSSC with 0.1% SDS at 50–65° C., including 0.5xSSC with 0.1% SDS at 55° C., or 2xSSC with 0.1% SDS at 65° C. One of skill in the art can readily devise equivalent conditions, for example, by substituting SSPE for SSC in the wash solution.

Typical highly stringent washing conditions include washing in a solution of 0.1x–0.2xSSC with 0.1% sodium dodecyl sulfate (SDS) at 50–65° C. In other words, polynucleotides encoding a variant ZTMPO-1 polypeptide hybridize with a polynucleotide having the nucleotide sequence of SEQ ID NO:1 (or its complement) under highly stringent washing conditions, in which the wash stringency is equivalent to 0.1x–0.2xSSC with 0.1 SDS at 50–65° C., including 0.1xSSC with 0.1% SDS at 50° C., or 0.2xSSC with 0.1% SDS at 65° C.

The present invention also contemplates ZTMPO-1 variant polypeptides that can be identified using two criteria: a determination of the similarity between the encoded polypeptide with the amino acid sequence of SEQ ID NO:2, and a hybridization assay, as described above. Such ZTMPO-1 variants include nucleic acid molecules (1) that hybridize with a nucleic acid molecule having the nucleotide sequence of SEQ ID NO:1 (or its complement) under stringent washing conditions, in which the wash stringency is equivalent to 0.5x–2xSSC with 0.1% SDS at 50–65° C., and (2) that encode a polypeptide having at least 80%, at least 90%, at least 95% or greater than 95% sequence identity to the amino acid sequence of SEQ ID NO:2. Alternatively, ZTMPO-1 variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1x–0.2xSSC with 0.1% SDS at 50–65° C., and (2) that encode a polypeptide having at least 80%, at least 90%, at least 95% or greater than 95% sequence identity to the amino acid sequence of SEQ ID NO:2.

As previously noted, the isolated polynucleotides of the present invention include DNA and RNA. Methods for preparing DNA and RNA are well known in the art. In general, RNA is isolated from a tissue or cell that produces large amounts of ZTMPO-1 RNA. Such tissues and cells are identified by Northern blotting (Thomas, *Proc. Natl. Acad. Sci. USA* 77:5201, 1980), an exemplary source being human testis tissue. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding ZTMPO-1 polypeptides are then identified and isolated by, for example, hybridization or PCR.

The polynucleotides of the present invention can also be synthesized using techniques widely known in the art. See, for example, Glick and Pasternak, *Molecular Biotechnology, Principles & Applications of Recombinant DNA*, (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are ZTMPO-1 polypeptides from other mammalian species, including murine, porcine, ovine, bovine, canine, feline, equine, and other primate polypeptides. Orthologs of human ZTMPO-1 can be cloned using information and compositions provided by the present invention in combination with conventional cloning techniques. For example, a cDNA can be cloned using mRNA obtained from a tissue or cell type that expresses ZTMPO-1 as disclosed herein. Suitable sources of mRNA can be identified by probing Northern blots with probes designed from the sequences disclosed herein. A library is then prepared from mRNA of a positive tissue or cell line. A ZTMPO-1-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human ZTMPO-1 sequence disclosed herein. Within an additional method, the cDNA library can be used to transform or transfect host cells, and expression of the cDNA of interest can be detected with an antibody to ZTMPO-1 polypeptide. Similar techniques can also be applied to the isolation of genomic clones.

Those skilled in the art will recognize that the sequence disclosed in SEQ ID NO:1 represents a single allele of human ZTMPO-1 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:2, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the ZTMPO-1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated ZTMPO-1 polypeptides that are substantially homologous to the polypeptides of SEQ ID NO:2 and their orthologs. The term "substantially homologous" is used herein to denote polypeptides having 50%, preferably 60%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs). Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. The present invention further includes nucleic acid molecules that encode such polypeptides. Methods for determining percent identity are described below.

Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant ZTMPO-1. The FASTA algorithm is described by Pearson and Lipman, Proc. Nat. Acad. Sci. USA 85:2444, 1988, and by Pearson, Meth. Enzymol. 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444, 1970; Sellers, SIAM J. Appl. Math. 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63, 1990.

FASTA can also be used to determine the sequence identity of nucleic acid molecules using a ratio as disclosed above. For nucleotide sequence comparisons, the ktup value can range between one to six, preferably from four to six.

Substantially homologous proteins and polypeptides are characterized as having one or more amino acid substitutions, deletions or additions. These changes are preferably of a minor nature, that is conservative amino acid substitutions and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the ZTMPO-1 polypeptide and the affinity tag. Preferred such sites include thrombin cleavage sites and factor Xa cleavage sites.

The present invention includes nucleic acid molecules that encode a polypeptide having one or more "conservative amino acid substitutions," compared with the amino acid sequence of SEQ ID NO:2. Conservative amino acid substitutions can be based upon the chemical properties of the amino acids. That is, variants can be obtained that contain one or more amino acid substitutions of SEQ ID NO:2, in which an alkyl amino acid is substituted for an alkyl amino acid in a ZTMPO-1 amino acid sequence, an aromatic amino acid is substituted for an aromatic amino acid in a ZTMPO-1 amino acid sequence, a sulfur-containing amino acid is substituted for a sulfur-containing amino acid in a ZTMPO-1 amino acid sequence, a hydroxy-containing amino acid is substituted for a hydroxy-containing amino acid in a ZTMPO-1 amino acid sequence, an acidic amino acid is substituted for an acidic amino acid in a ZTMPO-1 amino acid sequence, a basic amino acid is substituted for a basic amino acid in a ZTMPO-1 amino acid sequence, or a dibasic monocarboxylic amino acid is substituted for a dibasic monocarboxylic amino acid in a ZTMPO-1 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Other conservative amino acid substitutions are provided in Table 4.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The BLOSUM62 table is an amino acid substitution matrix derived from about 2,000 local multiple alignments of protein sequence segments, representing highly conserved regions of more than 500 groups of related proteins (Henikoff and Henikoff, *Proc. Natl. Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in a ZTMPO-1 gene can be introduced by substituting nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). The ability of such variants to promote proliferation and cardiac functions as will as other properties of the wild-type protein can be determined using a standard methods, such as the assays described herein. Alternatively, a variant ZTMPO-1 polypeptide can be identified by the ability to specifically bind anti-ZTMPO-1 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for ZTMPO-1 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related nuclear membrane bound proteins.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed ZTMPO-1 DNA and polypeptide sequences can be generated through DNA shuffling as disclosed by Stemmer, *Nature* 370:389–91, 1994 and Stemmer, *Proc. Natl. Acad. Sci. USA* 91:10747–51, 1994. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Preferred assays in this regard include cell proliferation assays and biosensor-based ligand-binding assays, which are described below. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 or that retain the receptor binding properties of the wild-type ZTMPO-1 protein. Such polypeptides may also include additional polypeptide segments as generally disclosed herein.

For any ZTMPO-1 polypeptide, including variants and fusion proteins, one of ordinary skill in the art can readily generate a fully degenerate polynucleotide sequence encoding that variant using the information set forth in Tables 1 and 2 above.

As used herein a fusion protein consists essentially of a first portion and a second portion joined by a peptide bond. In one embodiment the first portion consists of a polypeptide comprising a sequence of amino acid residues that is at least 80% identical in amino acid sequence to residues 1 through 876 of SEQ ID NO:2 and the second portion is any other polypetide. The other polypeptide may be alternative or additional domains from other members of the thymopoietin or emerin family, a signal peptide to facilitate secretion of the fusion protein, affinity tags, Ig domains or the like.

The ZTMPO-1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., N.Y., 1987.

In general, a DNA sequence encoding a ZTMPO-1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a ZTMPO-1 polypeptide into the secretory pathway of a host cell, a secretory signal sequence (also known as a leader sequence, signal sequence, prepro sequence or pre sequence) is provided in the expression vector. The secretory signal sequence may be derived from another secreted protein (e.g., t-PA) or synthesized de novo. The secretory signal sequence is operably linked to the ZTMPO-1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J*. 1:841–5, 1982), DEAE-dextran mediated transfection (Ausubel et al., ibid.), and liposome-mediated transfection (Hawley-Nelson et al., Focus 15:73, 1993; Ciccarone et al., *Focus* 15:80, 1993, and viral vectors (Miller and Rosman, *BioTechniques* 7:980–90, 1989; Wang and Finer, *Nature Med*. 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol*. 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al. , U.S. Pat. No. 5,162,222 and WIPO publication WO 94/06463. Insect cells can be infected with recombinant baculovirus vectors., which are commonly derived from *Autographa californica* multiple nuclear polyhedrosis virus (AcMNPV). DNA encoding the polypeptide of interest is inserted into the viral genome in place of the polyhedrin gene coding sequence by homologous recombination in cells infected with intact, wild-type AcMNPV and transfected with a transfer vector comprising the cloned gene operably linked to polyhedrin gene promoter, terminator, and flanking sequences. The resulting recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C. , 1994.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 9717450 and W09717451. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful as host cells within the present invention. Techniques for transforming these hosts and expressing foreign DNA sequences cloned therein are well known in the art (see, e.g., Sambrook et al., ibid.). When expressing a ZTMPO-1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co- transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant ZTMPO-1 polypeptides (or fusion or chimeric ZTMPO-1 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their binding properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., Glu-Glu tag) may be constructed to facilitate purification.

ZTMPO-1 polypeptides or fragments thereof may also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963.

Using methods known in the art, ZTMPO-1 polypeptides may be prepared as monomers or multimers; glycosylated or non-glycosylated; pegylated or non-pegylated; and may or may not include an initial methionine amino acid residue.

An in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–89, 1994; and Douglas and Curiel, *Science & Medicine* 4:44–53). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts may be incorporated into the viral DNA by direct ligation or by homologous recombination with a co-transfected plasmid. In an exemplary system, the essential E1 gene has been deleted from the viral vector, and the virus will not replicate unless the E1gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

The broad tissue distribution of ZTMPO-1 suggests it may play a critical role in biological processes of an organism and as such altered expression of ZTMPO-1 is likely involved in numerous pathologies associated with genetic and other human disease states, in particular those related to immunological, reproductive, cardiac and muscle pathologies, such as diabetes, muscular dystrophys, hematopoietic disorders, immune disorders, leukemias, hypertension and cardiac disorders and diseases. ZTMPO-1 polypeptides, agonists and antagonists have potential in both in vitro and in vivo applications.

ZTMPO-1 is expressed ubiquitously, many of those tissues are characterized by a high rate of cellular proliferation. ZTMPO-1 polypeptides would find use as regulators of cellular proliferation and/or differentiation. Proliferation and differentiation can be measured using cultured cells or in vivo by administering molecules of the present invention to the appropriate animal model. Suitable cultured cells, include but are not limited to, testicular, muscle, lymphatic and tumor cell lines which are all readily available to one skilled in the art from such sources as American Type Culture Collection, Rockville, Md. In particular, proliferation can be measured using cultured cardiac cells or in vivo by administering molecules of the present invention to the appropriate animal model. Generally, proliferative effects are seen as an increase in cell number, and may include inhibition of apoptosis as well as stimulation of mitogenesis. Cultured cells for use in these assays include cardiac fibroblasts, cardiac myocytes, skeletal myocytes, and human umbilical vein endothelial cells from primary cultures. Suitable established cell lines include: NIH 3T3 fibroblasts (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–32, 1992), and LNCap.FGC adenocarcinoma cells (ATCC No. CRL-1740). Cultured testicular cells include dolphin DB1.Tes cells (ATCC No. CRL-6258); mouse GC-1 spg cells (ATCC No. CRL-2053); TM3 cells (ATCC No. CRL-1714); TM4 cells (ATCC No. CRL-1715); and pig ST cells (ATCC No. CRL-1746). Mouse skeletal muscle (ATCC No. CRL-2174), human muscle (ATCC No. CRL-7522) and Raji, (Burkitt's human lymphoma, ATCC No. CCL86), Ramos (Burkitt's lymphoma cell line, ATCC No. CRL-1596), Daudi (Burkitt's human lymphoma, ATCC No. CCL213) and RPMI 1788 (a B lymphocyte cell line, CCL-156) all available from American Type Culture Collection, 10801 University Boulevard, Manassas, Va. 20110–2209. Cultured Assays measuring cell proliferation are well known in the art. For example, assays measuring proliferation include chemosensitivity to neutral red dye (Cavanaugh et al., *Investigational New Drugs* 8:347–54, 1990), incorporation of radiolabelled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–79, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–33, 1988). Additional methods can be found in the art, for example, *Current Protocols in Molecular Biology*, John Wiley and Sons, Inc., N.Y., 1997.

Assays measuring differentiation include, for example, measuring cell-surface markers associated with stage-specific expression of a tissue, enzymatic activity, functional activity or morphological changes (Watt, *FASEB*, 5:281–4, 1991; Francis, *Differentiation* 57:63–75, 1994; Raes, *Adv. Anim. Cell Biol. Technol. Bioprocesses*, 161–71, 1989). Bioassays and ELISAs are available to measure cellular response to ZTMPO-1, in particular are those which measure changes in cytokine production as a measure of cellular response (see for example, *Current Protocols in Immunology* ed. John E. Coligan et al., NIH, 1996).

In vivo assays are available for evaluating cardiac neogenesis or hyperplasia include treating neonatal and mature rats with the molecules of the present invention. The animals' cardiac function is measured as heart rate, blood pressure, and cardiac output to determine left ventricular function. Post-mortem methods for assessing cardiac decline or improvement include: increased or decreased cardiac weight, nuclei/cytoplasmic volume, and staining of cardiac histology sections to determine proliferating cell nuclear antigen (PCNA) vs. cytoplasmic actin levels (Quaini et al., *Circulation Res.* 75:1050–63, 1994 and Reiss et al., *Proc. Natl. Acad. Sci.* 93:8630–5, 1996.).

Cardiac defects related to conduction have been reported in patients having a deleted emerin gene (Emery, *J. Med. Genet.* 26:637–41, 1989). The resulting cardiac conduction defect is life threatening in these patients. Defects in the intrinsic conduction system can cause irregularities in the heart rhythm, such as arrhythmia and fibrillation. Tissue distribution and sequence similarities between emerin and ZTMPO-1 suggest that ZTMPO-1 may be involved in re-polarization of cardiac cell membranes. Localization of emerin to the desmosomes and fasciae adherentes suggests that association with the connection between epithelial cells accounts for the cardiac conduction defect when the gene is absent. ZTMPO-1 polypeptides and antagonists may influence cell-cell communication, either independently, or in conjunction with other proteins, such as emerin, and may regulate messages between cell membranes. To verify the presence of this capability in ZTMPO-1 polypeptides, agonists or antagonists of the present invention, such ZTMPO-1 polypeptides, agonists or antagonists are evaluated with respect to their ability to modulate cardiac conductance according to procedures known in the art. If desired, ZTMPO-1 polypeptide performance in this regard can be compared to emerin and may be evaluated in combination with emerin to identify synergistic effects. With respect to cardiac conductance, a resulting increase or decrease is measured by assessing voltage-dependent conductance, sodium or calcium ion flux in an appropriate assay system known in the art. Changes in the voltage conductance or in indicator substrates reflect the activities of ZTMPO-1 polypeptides on enhancing or inhibition cardiac conductance relative to a control not subjected to treatment. An electrocardiograph is used to monitor the electrical currents generated and transmitted through the heart. Changes in the electrocardiogram (ECG) tracing (wave pattern and/or timing) would indicate an alteration in the heart's conduction system. Therefore a return to a normal ECG pattern following ZTMPO-1 administration would indicate a re-establishment of a regular heart rhythm.

The invention also provides isolated and purified ZTMPO-1 polynucleotide probes or primers. Such polynucleotide probes can be RNA or DNA. DNA can be either cDNA or genomic DNA. Polynucleotide probes are single or double-stranded DNA or RNA, generally synthetic oligonucleotides, but may be generated from cloned cDNA or genomic sequences and will generally comprise at least 16 nucleotides, more often from 17 nucleotides to 25 or more nucleotides, sometimes 40 to 60 nucleotides, and in some instances a substantial portion, domain or even the entire ZTMPO-1 gene or cDNA. Probes and primers are generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nucleotides, more preferably 20–30 nucleotides. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, OR, and Amersham Corp., Arlington Heights, Ill., using techniques that are well known in the art. Preferred regions from which to construct probes include regions of homology with other thymopoietins and emerin as described herein, the ankyrin-like region, the calcium binding protein-like region, the signal sequence, and the like. Techniques for developing polynucleotide probes and hybridization techniques are known in the art, see for example, Ausubel et al., eds., *Current Protocols in Molecular Biology*, John Wiley and Sons, Inc., N.Y., 1991.

ZTMPO-1 polypeptides may be used within diagnostic systems to detect the presence of ZTMPO-1. The information derived from such detection methods would provide insight into the significance of ZTMPO-1 polypeptides in various diseases, and as a would serve as diagnostic tools for diseases for which altered levels of ZTMPO-1 are significant. Altered levels of ZTMPO-1 receptor polypeptides may be indicative of pathological conditions including cancer, cardiac and autoimmune disorders and infectious diseases.

In a basic assay, a single-stranded probe molecule is incubated with RNA, isolated from a biological sample, under conditions of temperature and ionic strength that promote base pairing between the probe and target ZTMPO-1 RNA species. After separating unbound probe from hybridized molecules, the amount of hybrids is detected.

Well-established hybridization methods of RNA detection include northern analysis and dot/slot blot hybridization (see, for example, Ausubel ibid. and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, ZTMPO-1 RNA can be detected with a nonradioactive hybridization method (see, for example, Isaac (ed.), *Protocols for Nucleic Acid Analysis by Nonradioactive Probes*, Humana Press, Inc., 1993). Typically, nonradioactive detection is achieved by enzymatic conversion of chromogenic or chemiluminescent substrates. Illustrative nonradioactive moieties include biotin, fluorescein, and digoxigenin.

ZTMPO-1 oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467, 1998).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)). PCR primers can be designed to amplify a sequence encoding a particular ZTMPO-1 domain or region of homology as described herein.

One variation of PCR for diagnostic assays is reverse transcriptase-PCR (RT-PCR). In the RT-PCR technique, RNA is isolated from a biological sample, reverse transcribed to cDNA, and the cDNA is incubated with ZTMPO-1 primers (see, for example, Wu et al. (eds.), "Rapid Isolation of Specific cDNAs or Genes by PCR," in *Methods in Gene Biotechnology*, CRC Press, Inc., pages 15–28, 1997). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or ZTMPO-1 anti-sense oligomers. Oligo-dT primers offer the advantage that various mRNA nucleotide sequences are amplified that can provide control target sequences. ZTMPO-1 sequences are amplified by the polymerase chain reaction using two flanking oligonucleotide primers that are typically at least 5 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled ZTMPO-1 probe, and examined by autoradiography. Additional alternative approaches include the use of digoxigenin-labeled deoxyribonucleic acid triphosphates to provide chemiluminescence detection, and the C-TRAK colorimetric assay.

Another approach is real time quantitative PCR (Perkin-Elmer Cetus, Norwalk, Conn.). A fluorogenic probe, consisting of an oligonucleotide with both a reporter and a quencher dye attached, anneals specifically between the forward and reverse primers. Using the 5' endonuclease activity of Taq DNA polymerase, the reporter dye is separated from the quencher dye and a sequence-specific signal is generated and increases as amplification increases. The fluorescence intensity can be continuously monitored and quantified during the PCR reaction.

Another approach for detection of ZTMPO-1 expression is cycling probe technology (CPT), in which a single-stranded DNA target binds with an excess of DNA-RNA-DNA chimeric probe to form a complex, the RNA portion is cleaved with RNase H, and the presence of cleaved chimeric probe is detected (see, for example, Beggs et al., *J. Clin. Microbiol.* 34:2985, 1996 and Bekkaoui et al., *Biotechniques* 20:240, 1996). Alternative methods for detection of ZTMPO-1 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161, 1996; Ehricht et al., *Eur. J. Biochem.* 243:358, 1997 and Chadwick et al., *J. Virol. Methods* 70:59, 1998). Other standard methods are known to those of skill in the art.

ZTMPO-1 probes and primers can also be used to detect and to localize ZTMPO-1 gene expression in tissue samples. Methods for such in situ hybridization are well-known to those of skill in the art (see, for example, Choo (ed.), *In Situ Hybridization Protocols*, Humana Press, Inc., 1994; Wu et al. (eds.), "Analysis of Cellular DNA or Abundance of mRNA by Radioactive In Situ Hybridization (RISH)," in *Methods in Gene Biotechnology*, CRC Press, Inc., pages 259–278, 1997 and Wu et al. (eds.), "Localization of DNA or Abundance of mRNA by Fluorescence In Situ Hybridization (RISH)," in *Methods in Gene Biotechnology*, CRC Press, Inc., pages 279–289, 1997).

Various additional diagnostic approaches are well-known to those of skill in the art (see, for example, Mathew (ed.), *Protocols in Human Molecular Genetics* Humana Press, Inc., 1991; Coleman and Tsongalis, *Molecular Diagnostics*, Humana Press, Inc., 1996 and Elles, *Molecular Diagnosis of Genetic Diseases*, Humana Press, Inc., 1996).

The invention also provides antagonists or inhibitors of ZTMPO-1 activity. Such antagonists would include anti-ZTMPO-1 antibodies, soluble ZTMPO-1 receptors, as well as other peptidic and non-peptidic agents (including ribozymes). Such antagonists would have use as research reagents for characterizing sites of ligand-receptor interaction. Antagonists would also find use in modulating cellular proliferation and differentiation such as in tumor growth and development. High levels of expression of ZTMPO-1 in testis tissue suggest a role in spermatogenesis. These ZTMPO-1 antagonists would be useful for inhibiting spermatogenesis and sperm activation. Such ZTMPO-1 antagonists can be used for contraception in humans and animals, and in particular, domestic and zoological animals and livestock, where they would act to prevent fertilization of an egg. Such ZTMPO-1 antagonists could be used, for instance, in place of surgical forms of contraception (such as spaying and neutering), and would allow for the possibility of future breeding of treated animals if desired. ZTMPO-1 antagonists could also be used to mediate immune response, for instance by boosting the humoral response in individuals at risk for an infectious disease or as a supplement to vaccination.

ZTMPO-1 can be used to identify inhibitors (antagonists) of its activity. Test compounds are transfected into cells or possibly added to the assays disclosed herein to identify compounds that inhibit the activity of ZTMPO-1. In addition to those assays disclosed herein, samples can be tested for inhibition of ZTMPO-1 activity within a variety of assays designed to measure receptor binding or the stimulation/inhibition of ZTMPO-1-dependent cellular responses. For example, ZTMPO-1-responsive cell lines can be transfected with a reporter gene construct that is responsive to a ZTMPO-1-stimulated cellular pathway. Reporter gene constructs of this type are known in the art, and will generally comprise a ZTMPO-1-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989).

Cyclic AMP response elements are reviewed in Roestler et al.,*J. Biol. Chem.* 263: 9063–6; 1988 and Habener,*Molec. Endocrinol.* 4:1087–94; 1990. Hormone response elements are reviewed in Beato, *Cell* 56:335–44; 1989. Candidate compounds, solutions, mixtures or extracts are tested for the ability to inhibit the activity of ZTMPO-1 on the target cells as evidenced by a decrease in ZTMPO-1 stimulation of reporter gene expression. Assays of this type will detect compounds that directly block ZTMPC-1 binding to cell-surface receptors, as well as compounds that block processes in the cellular pathway subsequent to receptor-ligand binding. In the alternative, compounds or other samples can be tested for direct blocking of ZTMPO-1 binding to receptor using ZTMPO-1 tagged with a detectable label (e.g., $^{125}$I, biotin, horseradish peroxidase, FITC, and the like). Within assays of this type, the ability of a test sample to inhibit the binding of labeled ZTMPO-1 to the receptor is indicative of inhibitory activity, which can be confirmed through secondary assays. Receptors used within binding assays may be cellular receptors or isolated, immobilized receptors.

ZTMPO-1 polypeptides can also be used to prepare antibodies that specifically bind to ZTMPO-1 epitopes, peptides or polypeptides. The ZTMPO-1 polypeptide or a fragment thereof serves as an antigen (immunogen) to inoculate an animal and elicit an immune response. Suitable antigens would be the ZTMPO-1 polypeptide encoded by SEQ ID NO:2 from amino acid number 1 to amino acid number 876, or contiguous 9 to 25 amino acid residue fragments thereof. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, (Ed.), *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a ZTMPO-1 polypeptide or a fragment thereof. The immunogenicity of a ZTMPO-1 polypeptide may be increased through the use of an adjuvant, such as alum (aluminum hydroxide) or Freund's complete or incomplete adjuvant. Polypeptides useful for immunization also include fusion polypeptides, such as fusions of ZTMPO-1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to ZTMPO-1 protein or peptide, and selection of antibody display libraries in phage or similar vectors (for instance, through use of immobilized or labeled ZTMPO-1 protein or peptide). Genes encoding polypeptides having potential ZTMPO-1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the ZTMPO-1 sequences disclosed herein to identify proteins which bind to ZTMPO-1. These "binding proteins" which interact with ZTMPO-1 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as ZTMPO-1 "antagonists" to block ZTMPO-1 binding and signal transduction in vitro and in vivo. These anti-ZTMPO-1 binding proteins would be useful for inhibiting binding.

Antibodies are determined to be specifically binding if: 1) they exhibit a threshold level of binding activity, and/or 2) they do not significantly cross-react with related polypeptide molecules. First, antibodies herein specifically bind if they bind to a ZTMPO-1 polypeptide, peptide or epitope with a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51: 660–72, 1949).

Second, antibodies are determined to specifically bind if they do not significantly cross-react with related polypeptides. Antibodies do not significantly cross-react with related polypeptide molecules, for example, if they detect ZTMPO-1 but not known related polypeptides using a standard Western blot analysis (Ausubel et al., ibid.). Examples of known related polypeptides are those disclosed in the prior art, such as known orthologs, and paralogs, and similar known members of a protein family. Moreover, antibodies may be "screened against" known related polypeptides, such as non-human ZTMPO-1, and ZTMPO-1 mutant polypeptides, to isolate a population that specifically binds to the inventive polypeptides. For example, antibodies raised to ZTMPO-1 are adsorbed to related polypeptides adhered to insoluble matrix; antibodies specific to ZTMPO-1 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984.

A variety of assays known to those skilled in the art can be utilized to detect antibodies and binding proteins which specifically bind to ZTMPO-1 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant ZTMPO-1 protein or polypeptide.

Antibodies to ZTMPO-1 may be used for tagging cells that express ZTMPO-1; for isolating ZTMPO-1 by affinity purification; for diagnostic assays for determining circulating levels of ZTMPO-1 polypeptides; for detecting or quantitating soluble ZTMPO-1 as marker of underlying pathology or disease; in analytical methods employing FACS; for screening expression libraries; for generating anti-idiotypic antibodies; and as neutralizing antibodies or as antagonists to block ZTMPO-1 binding in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to ZTMPO-1 or fragments thereof may be used in vitro to detect denatured ZTMPO-1 or fragments thereof in assays, for example, Western Blots or other assays known in the art.

Antibodies or polypeptides herein may also be directly or indirectly conjugated to drugs, toxins, radionuclides and the like, and these conjugates used for in vivo diagnostic or therapeutic applications. For instance, polypeptides or antibodies of the present invention may be used to identify or treat tissues or organs that express a corresponding anti-complementary molecule (receptor or antigen, respectively, for instance). More specifically, ZTMPO-1 polypeptides or anti-ZTMPO-1 antibodies, or bioactive fragments or portions thereof, can be coupled to detectable or cytotoxic molecules and delivered to a mammal having cells, tissues or organs that express the anticomplementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

Molecules of the present invention can be used to identify and isolate receptors involved in ZTMPO-1 binding. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

The molecules of the present invention will be useful regulators in multiple cellular organisms. The molecules of the present invention may used to modulate cellular proliferation and differentiation, for example spermatogenesis. In particular, certain proliferative disorders such as cancers may be amenable to such diagnosis, treatment or prevention. ZTMPO-1 would be useful in modulating the cell cycle such as during differentiation or in rapidly proliferating cells such as in tumor tissues. ZTMPO-1 would find application in a diverse array of tissues as testis, skeletal muscle, thyroid and adrenal gland for example.

Polynucleotides encoding ZTMPO-1 polypeptides are useful within gene therapy applications where it is desired to increase or inhibit ZTMPO-1 activity. If a mammal has a mutated or absent ZTMPO-1 gene, the ZTMPO-1 gene can be introduced into the cells of the mammal. In one embodiment, a gene encoding a ZTMPO-1 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a ZTMPO-1 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

The present invention also provides reagents for use in diagnostic applications. For example, the ZTMPO-1 gene, a probe comprising ZTMPO-1 DNA or RNA, or a subsequence thereof can be used to determine if the ZTMPO-1 gene is present on chromosome 12 or if a mutation has occurred. The emerin gene is not detected in samples from patients with Emery-Dreifuss muscular dystrophy, and is present in normal patients (Bione et al., *Nat. Genet.* 8:323–7, 1994 and Nagano et al., *Nat. Genet.* 12:254–9, 1996) and thus serves as a marker for the disease. Detectable chromosomal aberrations at the ZTMPO-1 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

Transgenic mice, engineered to express the ZTMPO-1 gene, and mice that exhibit a complete absence of ZTMPO-1 gene function, referred to as "knockout mice" (Snouwaert et al., *Science* 257:1083, 1992), may also be generated (Lowell et al., *Nature* 366:740–42, 1993). These mice may be employed to study the ZTMPO-1 gene and the protein encoded thereby in an in vivo system. Such mice could be used, for example, in breeding studies to determine the effect ZTMPO-1 has on spermatogenesis and sperm function as well as on conductivity of the heart.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a ZTMPO-1 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Determination of dose is within the level of ordinary skill in the art. The proteins may be administered for acute treatment, over one week or less, often over a period of one to three days or may be used in chronic treatment, over several months or years. Evaluation of therapeutic effect of ZTMPO-1 for cardiac applications can be done by looking for changes in ECG. Decreases in creatine kinase levels and a decrease in weakness would serve as indicators for changes in muscle wasting associated with muscular dystrophy.

The invention is further illustrated by the following non-limiting examples.

EXAMPLES

Example 1

Isolation of ZTMPO-1

Novel ZTMPO-1 encoding polynucleotides and polypeptides of the present invention were initially identified by querying an EST database. To identify the corresponding cDNA, two clones from which an identified EST was derived that were considered likely to contain the entire human ZTMPO-1 sequence were used for sequencing. Using a QIAwell 8 plasmid kit (Qiagen, Inc., Chatsworth, Calif.) according to manufacturer's instructions, a 5 ml overnight culture in LB+50 µg/ml ampicillin was prepared. The templates were sequenced on an Applied Biosystems™ model 377 DNA sequencer (Perkin-Elmer Cetus, Norwalk, Conn.) using the ABI PRISM™ Dye Terminator Cycle Sequencing Ready Reaction Kit (Perkin-Elmer Corp.) according to the manufacturer's instructions. Oligonucleotides ZC694 (SEQ ID NO:9), ZC976 (SEQ ID NO:10) and ZC447 (SEQ ID NO:14) were used as sequencing primers. Oligonucleotides ZC15976 (SEQ ID NO:11), ZC15485 (SEQ ID NO:12), ZC15526 (SEQ ID NO:13), Z15620 (SEQ ID NO:15) and ZC15823 (SEQ ID NO:16) were used to complete the sequence from the clones.

Sequencing reactions were carried out in a Hybaid Omni-Gene Temperature Cycling System (National Labnet Co., Woodbridge, N.Y.). Sequencher™ 3.0 sequence analysis software (Gene Codes Corporation, Ann Arbor, Mich.) was used for data analysis. The sequences from the two clones overlapped by 740 bp and contained the 3' end of the gene and the poly A tail. A third clone prepared as described above was sequenced resulting in the remaining 5' sequence. Oligonucleotides ZC447 (SEQ ID NO:14), ZC976 (SEQ ID NO:10), ZC16162 (SEQ ID NO:17), ZC16038 (SEQ ID NO:18), ZC16249 (SEQ ID NO:19), ZC16164 (SEQ ID NO:20), ZC16163 (SEQ ID NO:21), ZC16165 (SEQ ID NO:22) and ZC16037 (SEQ ID NO:23) were used in sequencing. Differences between the original EST sequences and the final sequence of ZTMPO-1 were detected. The lack of identity arose from ambiguity in the original EST sequences.

To confirm that the polynucleotide sequence encoding the initial methionine had been identified, a nested 5'RACE (rapid amplification of cDNA ends) was performed. Several Marathon™ cDNA libraries (human prostate, spleen, testis and uterus) were prepared using a Marathon cDNA kit (Clontech) according the manufacturer's instructions. For the first round PCR oligonucleotides AP1 (SEQ ID NO:24, supplied with the kit or synthesized) and ZC15527 (SEQ ID NO:25) were used as primers and the 5' RACE reaction was carried out at 94° C, for 2 minutes, followed by 25 cycles at 94° C. for 15 seconds, 61° C. for 20 seconds and 72° C. for 30 seconds, followed by a 1 minute extension at 72° C. The PCR products from the first round reaction were diluted 1/100 and used as templates for a second round of PCR using oligonucleotides AP2 (SEQ ID NO:32, supplied with the Marathon Kit or synthesized) and ZC15526 (SEQ ID NO:13) as primers. The PCR derived DNA fragments were resolved by gel electrophoresis, excised and ligated into the expression vector was the vector pCR2.1 (TA Cloning Kit, Invitrogen Inc., San Diego, Calif.) according to manufacturer's instructions. The sequence of the inserts was confirmed by sequence analysis using oligos ZC694 (SEQ ID NO:9) and ZC695 (SEQ ID NO:26) as primers, as described above and confirmed that the Met (amino acid residue 1 of SEQ ID NO:2) was indeed the start methionine. The resulting 2,754 bp polynucleotide (SEQ ID NO:1) had an open reading frame encoding an 876 amino acid residue protein sequence (SEQ ID NO:2) and was designated ZTMPO-1.

Example 2

Northern Blot Analysis of ZTMPO-1

Human Multiple Tissue Northern Blots (MTN I, MTN II and MTN III; Clontech) were probed to determine the tissue distribution of human ZTMPO1 expression. An approximately 218 bp PCR derived probe (SEQ ID NO:8) was amplified using EST clone EST934031 (SEQ ID NO:27) as a template and oligonucleotide ZC15521 (SEQ ID NO:28) and ZC15525 (SEQ ID NO:29) as primers. The amplification was carried out as follows: 1 cycle at 94° C. for 2 minutes, 30 cycles of 94° C. for 15 seconds, 65° C. 20 seconds and 72° C. 30 seconds, followed by 1 cycle at 72° C. for 1 minute. The PCR product was gel purified using the QIAquick method (Qiagen, Chatsworth, Calif.) and radioactively labeled using the Rediprime DNA labeling kit (Amersham, Arlington Heights, Ill.) both according to the manufacturer's suggestion. The probe was purified using a NUCTRAP push column (Stratagene). EXPRESSHYB (Clontech) solution was used for prehybridization and as a hybridizing solution for the Northern blots. Hybridization took place overnight at 65° C. using $4 \times 10^6$ cpm/ml of labeled probe. The blots were then washed in 2×SSC and 0.05% SDS at RT, followed by washes in 0.1×SSC and 0.1% SDS at 50° C. twice and at 55° C. once. Two transcripts of approximately 3.2 kb and 5 kb were seen in nearly all the tissues with the most predominant expression being in testis.

Example 3

Chromosomal Assignment and Placement of ZTMPO-1

ZTMPO-1 was mapped to chromosome 12 using the commercially available GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/ rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of ZTMPO-1 with the GeneBridge 4 RH Panel, 20 µl reactions were set up in a 96-well microtiter plate (Stratagene, La Jolla, Calif.) and used in a RoboCycler Gradient 96 thermal cycler (Stratagene). Each of the 95 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC15,487 (SEQ ID NO:6), 1 µl antisense primer, ZC 15486 (SEQ ID NO:7), 2 µl RediLoad (Research Genetics, Inc.), 0.4 µl 50×Advantage KlenTaq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 95° C. , 35 cycles of a 1 minute denaturation at 95° C. , 1 minute annealing at 62° C. and 1.5 minute extension at 72° C. , followed by a final 1 cycle extension of 7 minutes at 72° C. The reactions were separated by electrophoresis on a 2% agarose gel (Life Technologies, Gaithersburg, Md.).

The results showed that ZTMPO-1 maps 636.18 cR_3000 from the top of the human chromosome 12 linkage group on the WICGR radiation hybrid map. The proximal framework marker was D12S367. This positions ZTMPO-1 in the 12q24.33 region on the integrated LDB chromosome 12 map (The Genetic Location Database, University of Southhampton, WWW server: http://cedar.genetics.soton.ac.uk/public_html/).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising the amino acid sequence of SEQ ID NO:2.

2. An isolated polypeptide according to claim 1, wherein said polypeptide specifically binds with an antibody that specifically binds with a polypeptide consisting of the amino acid sequence of SEQ ID NO:2.

3. An isolated polypeptide according to claim 1, covalently linked to a moiety selected from the group consisting of affinity tags, radionucleotides, enzymes and fluorophores.

4. An isolated polypeptide according to claim 3, wherein said moiety is an affinity tag selected from the group consisting of polyhistidine, FLAG, Glu-Glu, glutathione S transferase and an immunoglobulin heavy chain constant region.

5. A fusion protein consisting essentially of a first portion and a second portion joined by a peptide bond, said first portion consisting of a polypeptide comprising the sequence of SEQ ID NO:2; and said second portion comprising another polypeptide that is not ZTMPO-1.

* * * * *